United States Patent
Oku et al.

(10) Patent No.: US 6,753,310 B1
(45) Date of Patent: Jun. 22, 2004

(54) NEOVASCULAR-SPECIFIC PEPTIDES

(75) Inventors: Naoto Oku, Shimizu (JP); Koichi Ogino, Naruto (JP); Dai Ishikawa, Tokushima (JP); Michinori Tanaka, Tokushima (JP); Takao Taki, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/807,278

(22) PCT Filed: Oct. 15, 1999

(86) PCT No.: PCT/JP99/05730

§ 371 (c)(1),
(2), (4) Date: Apr. 11, 2001

(87) PCT Pub. No.: WO00/23476

PCT Pub. Date: Apr. 27, 2000

(30) Foreign Application Priority Data

Oct. 16, 1998 (JP) ............................................ 10-295198
Jul. 8, 1999 (JP) ............................................ 11-194706

(51) Int. Cl.$^7$ ........................ A01N 37/18; A61K 38/00; A61K 39/00; C08G 69/26
(52) U.S. Cl. ........................ 514/2; 530/300; 424/184.1; 424/185.1; 528/332
(58) Field of Search ........................ 530/300; 424/184.1, 424/185, 185.1; 514/2; 528/332

(56) References Cited

U.S. PATENT DOCUMENTS 5,622,852 A * 4/1997 Korsmeyer .................. 435/325

FOREIGN PATENT DOCUMENTS

| WO | 98/12226 | 3/1998 |
| WO | 98/49322 | 11/1998 |
| WO | 99/29858 | 6/1999 |
| WO | 99/54456 | 10/1999 |
| WO | 99/55865 | 11/1999 |
| WO | 99/61476 | 12/1999 |

OTHER PUBLICATIONS

Nestor et al.(Geneseq Database, Accession No. AAP61443, EP182262–A, May 1986).*
Davis–Smith et al. (Issued Sequence Patent Database, US Patent No. 5,952,199, May 1996).*
Guild et al. (Geneseq Database, Accession No. AAR52123, EP592106–A1, Apr. 1994.*
MSNBC News Services, "Mixed results on new cancer drug", Nov. 9, 2000.*
Gura (Science, v278, 1997, pp. 1041–1042).*
Sato TN, et al., "Tei–1 and tie–2 defube another class of putative receptor tyrosinekinase genes expressed in early embryonic vascular system", Proc. Natl. Acad. Sci. USA (1993), vol. 90, No. 20, pp. 9355–9358.
Wadih et al, *Science*, 279(5349):377–380 (1998).
Thorpe et al, *J. of Controlled Release, Elseier Science Publishers B. V. Amsterdam, N.L.*, 48(2–3):277–288 (1997).
Ohizumi et al, *Biochem. and Biophys., Res. Comm.*, 236(2):493–496 (1997).
Gho et al, *J. of Biological Chem.*, 272(39):24294–24299 (1997).

* cited by examiner

*Primary Examiner*—Gary B. Nickol
(74) *Attorney, Agent, or Firm*—Sughrue Mion, PLLC

(57) ABSTRACT

Angiogenesis-specific peptides which home selectively to neovascular tissues and comprise one of the peptides having the amino acid sequences shown in SEQ ID NOS: 1 to 17 and dendrimers thereof. These peptides are applicable to DDS preparations whereby drugs can be transported selectively to target cancer tissues and are useful as diagnostics for cancer, remedies for cancer, etc. which contribute to the improvement in the therapeutic effects on cancer.

2 Claims, 15 Drawing Sheets

Number of days after tumor implantation (days)

Number of days after tumor implantation (days)

NEOVASCULAR-SPECIFIC PEPTIDES

CROSS-REFERENCE TO RELATED APPLICATIONS

This application is a 371 of PCT/JP99/05730, filed Oct. 15, 1999, the disclosure of which is incorporated herein by reference.

TECHNICAL FIELD

The present invention relates to peptide molecules homing specifically to neovascular tissues and, more particularly, to angiogenesis-specific (neovascular-specific) peptides which function as ligands to neovascular endothelial cells of cancer tissues, for instance, and are useful as molecular drugs and applicable to drug delivery system (DDS) preparations enabling selective drug delivery to target tissues and can contribute to improvements in the therapeutic effects on cancer.

BACKGROUND ART

One of the factors which make cancer chemotherapy difficult to do successfully are the fact that the drug administered kills or damages not only the target cancer tissues but also normal tissues, causing adverse effects. As means of minimizing such side effects and achieving improvements in the efficacy of anticancer agents, drug delivery systems (DDSs) have attracted attention in the field of cancer therapy.

The DDSs mentioned above which are targeted at cancer may be classified into two types, namely passive targeting type and active targeting type. Since neovascular tissues show increased vascular permeability as compared with pre-existing vessels, a preparation of the long retention-in-blood type is gradually accumulated in cancer tissues. Passive targeting is the targeting utilizing that property. A passive targeting preparation in which liposomes are used has already been used in Europe and America in the treatment of Kaposi's sarcoma. On the other hand, an active targeting preparation is designed, by modifying the drug with an antibody or some other ligand capable of binding to a cell surface marker, such as a protein, highly expressed in cancer cells or tissues surrounding the same, so that the drug can be delivered actively and selectively to cancer cells, without causing harmful effects on normal tissues.

In the field of current cancer therapy, angiogenesis has become a focus of attention. The term "angiogenesis" refers to the development of blood vessels within cancer tissues which parallel the growth of tumors in the procession of cancer. Thus, for active proliferation of cancer cells and growth and metastasis of cancer tissues, it is important that blood vessels, which are organs serving to feed nutrients and oxygen and eliminate metabolites and waste materials, be newly constructed. In this respect, the growth of cancer tissues can be highly dependent on angiogenesis.

It is considered that when this angiogenesis is inhibited, the growth and metastasis of cancer tissues, might be prevented. From this point of view, it is desired in the art that a cancer therapy targeted on neovascular tissues, in particular an active targeting preparation (DDS preparation), be developed.

DISCLOSURE OF INVENTION

A substance capable of serving as a ligand for neovascular endothelial cells in a cancer tissue, if identified, isolated and made available, will lead to its application in DDS preparations and to further improvements in the efficiency of cancer therapy.

It is an object of the present invention to provide such a novel ligand.

Another object of the invention is to provide a substance capable of inhibiting angiogenesis.

In the course of intensive investigations made for the above purposes, the inventors obtained the findings mentioned below. Thus, the inventors first induced the formation of tumor neovascular tissues in the mouse dorsum by the chamber ring method (Folkman, J., et al., J. Exp. Med., 133, 275–288 (1971)). Then, a random peptide-displaying phage constructed by inserting random DNAs into the phage+ coat protein pIII gene to thereby enable the expression of random peptides having a 15-amino-acid sequence on the phage shell was administered to the mice. Thereafter, the mice were frozen with liquid nitrogen, skin portions bearing neovascular tissues were dissected, homogenized in a culture medium containing a protease inhibitor, washed and centrifuged, and the phage was thus recovered from neovascular tissues. The phage was infected into *Escherichia coli*, which was mass-cultured. After isolation and purification, there was obtained a phage capable of expressing a peptide to be accumulated in the neovascular tissue endothelium and serve as a ligand. For a plurality of phages obtained in that manner, the peptides expressed by them were sequenced.

Then, for selecting a phage expressing a peptide having high affinity for neovascular tissues, each phage obtained in the above manner was administered into the tail vein of tumor-bearing mice prepared by tumor cell implantation. The mice were frozen in the same manner as above, tumor tissues were dissected, and the phages were isolated and purified from the materials obtained and used to infect *Escherichia coli*, followed by cultivation. And, for each phage, colony-forming units were counted, with the phage before selection being used as a control. The affinity for neovascular tissues was calculated in terms of the ratio of number of phages administered to the tail vein to number of accumulated phages per 100 mg of tumor tissue. In this way, candidate peptides for ligands having high affinity for neovascular tissues were obtained.

Further, the inventors synthesized the above peptides, dendrimers thereof, partial peptides thereof and the like, and confirmed that these peptides actually show antitumor effects and, at the same time, confirmed that liposomes modified with the peptides, in particular these peptides which contains the sequence Trp-Arg-Pro and the sequence Pro-Arg-Pro, show significantly higher levels of distribution in the tumor as compared with the control.

The present invention was accomplished on the basis of these findings.

The invention provides an angiogenesis-specific peptide selectively homing to neovascular tissues, which comprises one of the members listed below under (a) and (b):

(a) a peptide having one of the amino acid sequences shown in SEQ ID NO: 1 to 11, or a dendrimer thereof, (b) a peptide having an amino acid sequence derived from any of the amino acid sequences of the peptide defined above under (a) by substitution, deletion or addition of one or a plurality of amino acid residues and having affinity for neovascular tissues, or a dendrimer thereof.

In particular, the invention provides an angiogenesis-specific peptide as mentioned above which is a peptide having one of the amino acid sequences shown in SEQ ID NO: 1 to 11, or a dendrimer thereof; more preferably, an angiogenesis-specific peptide as mentioned above which is a peptide having one of the amino acid sequences shown in SEQ ID NO: 1, 5 and 6, or a dendrimer thereof; an angiogenesis-specific peptide as mentioned above which is a dendrimer comprising a plurality of peptides which are the same or different and have one of the amino acid sequences shown in SEQ ID NO: 1 to 11; an angiogenesis-specific peptide as mentioned above which is a peptide having one of the amino acid sequences shown in SEQ ID NO: 12 to 17, or a dendrimer thereof; and an angiogenesis-specific peptide as mentioned above which is a peptide having one of the amino acid sequences shown in SEQ ID NO:19, 21, 23–25 and 28–32, or a dendrimer thereof.

The invention further provides an angiogenesis-specific peptide as mentioned above which homes selectively to neovascular tissues developed in cancer/tumor tissues, for example sarcoma or melanoma.

The invention still further provides an anticancer composition and a cancer metastasis inhibitor composition, each of which comprises, as an active ingredient, at least one of the above angiogenesis-specific peptides, preferably at least one peptide having one of the amino acid sequences shown in SEQ ID NO:1, 5, 6, 13–17, 19, 21, 23–25 and 28–32 or dendrimer thereof, together with a pharmaceutical carrier therefor.

The invention further provides a liposome preparation which comprises, as active ingredients, at least one of the above angiogenesis-specific peptides, preferably at least one peptide having one of the amino acid sequences shown in SEQ ID NO:15–17, or dendrimer thereof, and an anticancer agent or cancer metastasis inhibitor, together with a pharmaceutical carrier therefor.

The invention further provides a method of combating cancer/tumor or inhibiting cancer metastasis which comprises administering an effective amount of at least one of the above angiogenesis-specific peptides to a patient, in particular a method of combating cancer/tumor or inhibiting cancer metastasis which comprises administering an effective amount of at least one peptide having one of the amino acid sequences shown in SEQ ID NO:1, 5, 6, 13–17, 19, 21, 23–25 and 28–32, or at least one dendrimer thereof, to a patient.

The invention further provides a method of combating cancer/tumor or inhibiting cancer metastasis which comprises administering a liposome preparation comprising, as active ingredients, at least one peptide having one of the amino acid sequences shown in SEQ ID NO:15–17, or at least one dendrimer thereof, and an anticancer agent or cancer metastasis inhibitor, together with a pharmaceutical carrier therefor, to a patient.

Hereinafter, the amino acids, peptides, base sequences, nucleotides and the like, when indicated by symbols, are indicated according to the recommendations of the IUPAC-IUB or the "Guideline for preparing specifications etc. containing nucleotide sequences or amino acid sequences" (edited by the Japanese Patent Office) and the conventional symbols used in the relevant field of art.

Specific examples of the angiogenesis-specific peptide of the invention are these having the amino acid sequences shown in SEQ ID NO:1 to 11 which are obtained by the methods shown in the examples given later herein.

In the following, the identification and affinity for neovascular tissues of the angiogenesis-specific peptide of the invention are described.

For identifying the angiogenesis-specific peptide of the invention, the molecular library screening technique can be employed. A preferred example of the library is a phage-displayed library. Such a library may be a commercially available one. The random peptide-displaying phage in said library is utilized for causing expression of a large number of peptides, which can be screened in vitro using a specific target molecule or objective cell, for identifying a peptide specifically binding to the target molecule or cell. The screening using such a library is utilized to identify ligands or various antibodies specifically binding to various cell surface receptors. For the method of constructing such a phage-displayed library and the method of in vitro screening, reference is made to the method of Scott and Smith (Scott, J. M. and Smith, G. P., Science, 249, 386–390 (1990); Smith, G. P. and Scott, J. K., Methods in Enzymology, 217, 228–257 (1993)).

More preferable method to be used in identifying the angiogenesis-specific peptide of the invention as a molecule capable of homing to neovascular tissues is, for example, the method of Ruoslahti et al. described in JP Kohyo H10-502674 (corresponding to U.S. Pat. No. 5,622,699) which identifies a molecule homing to an organ or tissue. The method identifies a molecule homing specifically to one, two or three selected organs or tissues using in vivo panning for screening a library of molecules potentially homing to an organ or organs and can be carried out in the following manner.

Thus, first, random DNAs are introduced into a known phage library, and the thus-obtained diluted mixture of the phage library is administered into the tail vein of a mouse, for instance. One to four minutes later, the mouse is rapidly frozen in liquid nitrogen. For phage recovery, the dead body is thawed, the desired organ or tissue is collected and homogenized in a culture medium containing a protease inhibitor and the preparation obtained is washed several times with an ice-cooled culture medium containing 1% bovine serum albumin and used to infect *Escherichia coli*. The phage-infected *Escherichia coli* is cultured in a tetracycline-containing medium for several hours and then used to precoat a tetracycline-containing agar plate. The phage-containing colonies recovered are cultured on an appropriate medium, and phages are isolated and purified. And, the second and subsequent biopanning procedures are carried out. This second, and subsequent, biopanning can be carried out in the same manner as mentioned above using the phages obtained in the above manner. Thus, a DNA coding for a peptide expressed by a desired and selected phage can be obtained. By sequencing the DNA obtained, the molecule homing to the desired organ or tissue can be identified.

The DNA sequencing can be readily carried out by a method well known in the art, for example by the dideoxy method [Proc. Natl. Acad. Sci. USA, 74, 5463–5467 (1977)] or the Maxam-Gilbert method [Methods in Enzymology, 65, 499 (1980)]. Such base sequence determination can also be carried out with ease using a commercial sequencing kit or the like.

As a method of detecting the affinity of a molecule homing to an organ or tissue, the following method, for instance, can be employed. Thus, in the above-mentioned method of identifying a molecule homing specifically to an organ or tissue, the organ- or tissue-specific peptide-expressing phage obtained and the phage before selection are administered into the tail vein of experimental animals, and phage-containing colony forming units are counted by the same method as mentioned above. By evaluating the ratio of number of accumulated phages to number of phages administered into the tail vein per 100 mg of the target organ or tissue, for instance, the affinity of the molecule homing to the desired organ or tissue can be detected.

Further, the homing specificity of a peptide can be confirmed by the competitive method, for instance, by selecting one of peptides homing to the target organ or tissue, synthesizing said peptide, purifying the same by high performance liquid chromatography (HPLC) and examining the effects of several peptide phages containing a phage expressing the same peptide as the above synthetic peptide and homing to the target organ or tissue by simultaneous administration with the synthetic peptide (cf. JP Kohyo H10-502674; U.S. Pat. No. 6,522,699).

The details of the methods of identifying the angiogenesis-specific peptide of the invention and detecting the affinity for neovascular tissues thereof are as shown later herein in the examples. The angiogenesis-specific peptide of the invention as identified by in vivo panning in mice as shown later in an example can bind to the neovascular tissues of solid tumors in human or other mammalian species. The peptide of the invention which binds to a target molecule occurring in the neovascular tissue grown in mice can bind to the corresponding molecule in the neovascular tissues of tumors in human or other mammalian bodies. Further, the peptide of the invention can specifically bind in vitro to a sample obtained from a patient. From these facts, it can be confirmed that the peptide of the invention has the ability to bind to the corresponding molecule of the human patient.

The vascularization in cancer tissues is characterized in that the formation of new blood vessels supporting the growth occurs continuously; it is thus distinguished from ordinary histological vascularization (Folkman, Nat. Med., 1, 27–31 (1995); Rak, Anticancer Drugs, 6, 3–18 (1995)). Therefore, the peptide of the invention specifically homing to neovascular tissues as identified by in vivo panning can be used as an angiogenesis-inhibiting factor against cancer.

On the other hand, the peptide of the invention, which specifically homes to neovascular tissues, is very low in the possibility of producing adverse effects on normal healthy organs and tissues.

Further, since the peptide of the invention homes not to cancer cells but to the neovascular tissue, the possibility of its acquiring drug resistance such as the case with anticancer agents is considered to be low.

The peptide of the invention which homes specifically to neovascular tissues can further be used targeting other new blood vessels such as those occurring in inflammatory tissues or regenerated or injured tissues. Further, neovascularization occurs in uterine tissues as well, and the peptide of the invention is considered to be able to bind to such uterine tissues and is expected to exert an influence on such diseases as hysteromyoma.

The peptide of the invention as identified and established in the above manner includes the peptides specified by SEQ ID NO:1 to 11, and these are all characterized by having the property of homing to neovascular tissues.

The peptide of the invention includes peptides having one of the amino acid sequences shown in SEQ ID NO:1 to 11 as well as peptides comprising an amino acid sequence derived from said amino acid sequences by modification through substitution, deletion or addition of one or a plurality of amino acid residues and having affinity for neovascular tissues, namely the property of homing to neovascular tissues.

The extent and positions) of "substitution, deletion or addition" of an amino acid(s) are not restricted provided that the modified proteins are equivalents having the same properties as the angiogenesis-specific peptides respectively comprising the amino acid sequences shown in SEQ ID NO:1 to 11. While the above amino acid sequence modification (mutation) or the like may occur naturally, for example upon mutation or posttranslational modification, artificial modification based on the nature-derived gene is also possible. The invention includes all modified peptides having the above characteristics, irrespective of cause or means of such modification/mutation.

The peptide of the invention further includes homologs of the peptides having the amino acid sequences shown in SEQ ID NO:1 to 11. The homologs include mammalian proteins, for example proteins of the human, horse, sheep, cattle, dog, monkey, cat, bear or rodent (e.g. rat, rabbit) origin, which have the same activities as the peptides having the amino acid sequences shown in SEQ ID NO:1 to 11.

Examples of the peptide of the invention which have an modified amino acid sequences are these having sequences derived from the sequences shown in SEQ ID NO:1, 5 and 6 by allowing the sequences occurring therein overlapping in part, for example Pro-Arg-Pro and Trp-Arg-Pro, to remain and substituting, for an amino acid residue or residues of the remaining amino acid sequence, another amino acid residue or other amino acid residues, deleting an amino acid residue or residues or adding some other amino acid residue or residues; these having sequences derived from the sequence shown in SEQ ID NO:2 by substituting other amino acid resides for the 2nd and 8th amino acid residues; and these having sequences derived from the sequence shown in SEQ ID NO:11 by allowing the amino acid sequence portion from the 4th to the 11th amino acid residue alone to remain and deleting the remaining residues.

Specific examples of the peptide of the invention as derived by partial modification of one of the amino acid sequences are the peptide comprising 12 amino acid residues as shown in SEQ ID NO:19; the peptides comprising 8 amino acid residues as shown in SEQ ID NO:12 to 14 and 21; the peptides comprising 5 amino acid residues as shown in SEQ ID NO:15 to 17 and 23–25; the peptides comprising 4 amino acid residues as shown in SEQ ID NO:28 to 31; and the peptide comprising 3 amino acid residues (Trp-Arg-Pro) as shown in SEQ ID NO:32.

More specifically, the peptide shown in SEQ ID NO:12, for instance, is derived from SEQ ID NO:11 by retaining only the portion from the 4th to 11th amino acid residue. The peptide shown in SEQ ID NO:13 is derived from the sequence comprising 15 amino acid resides as shown in SEQ ID NO:5 by retaining 8 amino acid residues from the N terminus and deleting the remaining 7 amino acid residues. The peptide shown in SEQ ID NO:14 has a sequence of 8 amino acid residues as a result of deletion of the 7 amino acid residues from the N terminus of the amino acid sequence shown in SEQ ID NO:6. The peptide shown in SEQ ID NO:15 has the sequence from the 2nd to the 6th amino acid residues of the amino acid sequence shown in SEQ ID NO:5. The peptide shown in SEQ ID NO:16 has the sequence from the 9th to the 13th amino acid residues of the amino acid sequence shown in SEQ ID NO:6. The peptide shown in SEQ ID NO:17 is derived from the 1st to 4th amino acid residues of the amino acid sequence shown in SEQ ID NO:1 by addition of Ala to the N terminus thereof.

Among the peptides which the present invention includes, peptides having at least two cysteine residues, for example the peptide having the amino acid sequence shown in SEQ ID NO:11, are considered to spontaneously cyclize, and such cyclic peptides are also active in some instances even when they occur in the linear form and, therefore, one or both of the cysteine residues in said peptides do not exert a significant influence on the homing characteristic of the peptides, hence can be deleted. Such phenomenon is supported, for example, by the report by Koivunen et al. (J. Biol. Chem., 268, 20205–20210 (1993)). A specific example of such peptide having an amino acid sequence resulting from deletion is as shown in SEQ ID NO:12. Peptides having such a partly deleted amino acid sequence, too, if they have the above-mentioned property of homing to neovascular tissues, fall within the scope of the invention.

As used herein, the term "angiogenesis-specific peptide" or "peptide of the invention" includes peptides having a modified amino acid sequence derived from any of the above-mentioned amino acid sequences as shown in SEQ ID NO:1 to 11 as standards, for example partial peptides derived therefrom by deletion of a partial amino acid sequence.

The angiogenesis-specific peptide of the invention includes peptides having one of the amino acid sequences shown in SEQ ID NO:1 to 11, peptides whose amino acid sequence is derived from said amino acid sequences by modification and which has the property of homing to neovascular tissues, and further dendrimers of these peptides.

The term "dendrimer" is used herein to mean a peptide known as a macromolecule having a specific composition, a specific molecular weight, and a spherical or three-dimensional structure and also known as a multiple antigen peptide (MAP). The synthesis thereof can be carried out, for example, starting with a chemical structure nucleus having a plurality of functional groups, causing a branch (repeating unit) terminally having a plurality of the same functional groups as these of the chemical structure nucleus to be bound to each functional group of the nucleus and further introducing the same repeating unit one by one into the terminal functional groups. The details are described, for example, in JP Kohyo S60-500295, JP Kokai S63-99233, JP Kokai H03-263431, U.S. Pat. No. 4,507,466, U.S. Pat. No. 4,568,737, Poloymer Journal, vol. 17, page 117 (1985), Tomalia, et al., Angewandte Chem. Int. Engl., vol. 29, pages 138–175 (1990), and Macromolecules, vol. 25, page 3247 (1992).

Dendrimers as mentioned above comprise a core moiety serving as a starting nucleus for a spherical appearance with a branched or stellar configuration, internal layers (generations of ramifications) constituted of repeating units radially extend outwardly from the starting core, and an external surface comprising activated functional groups bound to respective outermost termini of respective generations or branches. The size, shape and reactivity of a dendrimer can be adjusted by selecting the starting core moiety, the generation of the dendrimer and the composition and structure of the repeating unit to be used for each generation.

Dendrimers differing in size can be obtained by increasing the generations employed and, for their production, reference may be made to U.S. Pat. No. 4,694,064, for instance.

Typical dendrimers include, for example, dendrimers comprising a nitrogen atom as the core moiety serving the starting nucleus, repeating units having the structure —$CH_2CH_2CONHCH_2CH_2$— bound to the core and activated functional groups which are bound to the outermost terminal amino groups of each branches and whose constituents are angiogenesis-specific peptides of the invention as shown in SEQ ID NO:1 to 17; and dendrimers shown later in the examples which comprise an amino acid, such as lysine, arginine, glutamic acid or aspartic acid, as the core moiety, the same amino acids as mentioned above as the repeating units directly bound to the core moiety, and angiogenesis-specific peptides of the invention having an amino acid sequence selected from among SEQ ID NO:1 to 17 or angiogenesis-specific peptides of the invention having an amino acid sequence selected from among SEQ ID NO:19, 21, 23–25 and 28–32 as the activated functional groups.

Dendrimers with an angiogenesis-specific peptide of the invention bound to the outermost terminus of each branch can be produced by the solid-phase synthetic method described later herein using a dendrimer having a nitrogen atom serving as the starting core moiety, which is commercially available from Polysciences, Inc., 400 Vally Road, Warrington, Pa., 18976, U.S.A., for instance. Similarly, dendrimers comprising angiogenesis-specific peptides of the invention bound to the outermost terminus of each branch can be produced by the solid-phase synthetic method described later herein using lysine as the core moiety serving as the starting site, and the same amino acid lysine as the repeating unit directly bound to the core moiety. In producing the dendrimer, a $Fmoc_8$-$Lys_4$-$Lys_2$-Lys-β-Ala-Alko resin produced by Watanabe Kagaku Kogyo can be used. In the above process, it is also possible to produce dendrimers containing constituents having anticancer activity either in lieu of part of the angiogenesis-specific peptides of the invention to be bound to the outermost terminus of each branch or in the form bound to the core moiety.

The dendrimers mentioned above each can be synthesized, for example, in the following manner. Thus, dendrimers can be obtained by condensing a resin for solid-phase peptide synthesis, via a spacer or without any spacer, with an α,ω-diamino acid, as a repeating unit, wherein two amino groups are protected with the same or different protective groups, followed by deprotection and by repetitions of the condensation of the repeating unit, each time followed by deprotection.

Usable as the resin for solid-phase peptide synthesis are resins generally used in peptide synthesis, such as polystyrene, polyacrylamide, polystyrene-polyethylene glycol and like resins. These resins are used with terminally additional groups of a chloromethyl, 4-(hydroxymethyl) phenoxy, 4-((α-2',4'-dimethoxyphenyl)-9-fluorenylmethoxycarbonylaminomethyl)phenoxy or the like.

As the spacer, one amino acid or a plurality of amino acids can be used. Examples of the α,ω-diamino acids are lysine, ornithine, 1,4-diaminobutyric acid, 1,3-diaminopropionic acid and the like. The protective groups include a Boc group, an Fmoc group, a Z group and the like. Therefore, the functional groups are an amino group, a carboxyl group, a hydroxy group and the like. When the procedure comprising repeating unit condensation and deprotection is repeated n times, the number of branches becomes 2n. Specific number of the branches is 2 to 16.

Such dendrimers can be purified by ordinary techniques, for example by a chromatographic procedure using a resin capable of size exclusion in a matrix form, such as Sephacryl S-300 (product of Pharmacia), for instance.

The dendrimer peptide thus obtained selectively homes to neovascular tissues proper owing to the occurrence of the angiogenesis-specific peptide of the invention in its branch moieties and produces an angiogenesis inhibiting effect, whereby the desired anticancer effect and cancer metastasis preventing effect can be produced. When it is administered with a known agent having anticancer activity packed therewithin, the dendrimer peptide can allow the agent to act on the target angiogenic site alone, hence it is advantageous in that it can render the anticancer agent less capable of producing side effects.

The angiogenesis-specific peptide to be present in the branch moieties of the above dendrimer peptide are not always one and the same peptide for each branch but may include a plurality of peptides differing in amino acid sequence. As examples, there may be mentioned the combined binding, to different branch moieties, of two or more of the peptides respectively having the amino acid sequences shown in SEQ ID NO:1, SEQ ID NO:5 and SEQ ID NO:6, or of two or more of the peptides respectively having the 15 amino acid sequences shown in SEQ ID NO:1–11, the peptides respectively having the 8 amino acid sequences shown in SEQ ID NO:12–14 and 21, the peptides respectively having the 5 amino acid sequences shown in SEQ ID NO:15–17 and 23–25, the peptides respectively having the 4 amino acid sequences shown in SEQ ID NO:28–31, and the peptide having the 3 amino acid sequence shown in SEQ ID NO:32. Such dendrimers can show improved stability in the blood and tissues of the administration target, improved specific activity of each bound molecule, and the like.

The angiogenesis-specific peptide of the invention can be synthesized by a common chemical synthetic method based on the amino acid sequence thereof. Said method includes liquid-phase and solid-phase methods of peptide synthesis. More detailedly, such methods of peptide synthesis include the stepwise elongation technique effecting chain extension using amino acids one by one based on the amino acid sequence information, and the fragment condensation technique comprising synthesizing fragments composed of several amino acids in advance and then coupling the fragments together. Either technique can be used in synthesizing the angiogenesis-specific peptide of the invention.

The method of condensation for use in the above peptide synthesis may be any of various known methods. The specific examples are the azide method, mixed acid anhydride method, DCC method, activated ester method, oxidation/reduction method, DPPA (diphenylphosphoryl azide) method, DCC+additive (1-hydroxybenzotriazole, N-hydroxy-succinimide, N-hydroxy-5-norbornene-2,3-dicarboximide or the like) method and Woodward method. The solvent to be used in each of these methods can adequately be selected from among those ordinary ones which are well known to be useful in this kind of peptide condensation reaction. Examples of the solvents include N-methylpyrrolidone (NMP), dimethylformamide (DMF), dimethyl sulfoxide (DMSO), hexamethylphosphoramide, dioxane, tetrahydrofuran (THF), ethyl acetate, etc., and mixture thereof.

In the peptide synthesis reaction, the carboxyl group of an amino acid or peptide not involved in the reaction can be protected generally by esterification, for example as a lower alkyl ester, such as methyl ester, ethyl ester or tert-butyl ester, an aralkyl ester such as benzyl ester, p-methoxybenzyl ester or p-nitrobenzyl ester, or the like. As for the amino acids having a functional group on the side chain, the hydroxyl group of Tyr, for instance may be protected with an acetyl, benzyl, benzyloxycarbonyl, tert-butyl or like group; such protection is not always necessary, however. Further, the guanidino group of Arg, for instance can be protected with an appropriate protective group such as nitro, tosyl, 2-methoxybenzene-sulfonyl, methylene-2-sulfonyl, benzyloxycarbonyl, isobornyloxycarbonyl or adamantyloxycarbonyl. The elimination reaction of such protective groups in the amino acids, peptides and final product angiogenesis-specific peptide of the invention which have those protective groups can be carried out by conventional methods, for example by catalytic reduction or using liquid ammonia/sodium, hydrogen fluoride, hydrogen bromide, hydrogen chloride, trifluoroacetic acid, acetic acid, formic acid, methane-sulfonic acid or the like.

The thus-obtained angiogenesis-specific peptide of the invention can appropriately be purified by methods generally used in the field of peptide chemistry, for example by ion exchange resins, partition chromatography, gel chromatography, affinity chromatography, high performance liquid chromatography (HPLC), countercurrent distribution or the like.

The angiogenesis-specific peptides of the invention obtainable in the above manner (inclusive of dendrimers thereof; hereinafter the same shall apply) have the ability to specifically home to neovascular tissues and are themselves useful as angiogenesis inhibitors. Further, the angiogenesis-specific peptides of the invention have the ability to specifically home to neovascular tissues of cancer tissues and therefore can be used as ligands for cancer tissues, for example in combination with anticancer agents, such as cancer chemotherapeutic agents, bound thereto.

Examples of various target cancer/tumor diseases include melanoma, carcinoma of colon and rectum, ovarian cancer, liver cancer, mammary cancer, brain tumor, renal cancer, pancreatic cancer, cervix cancer, esophageal cancer, lung cancer, gastric cancer and the like.

As the anticancer agents or components having anticancer activity which can be used as agents in combination with the angiogenesis-specific peptides of the invention, the following various cancer chemotherapeutic agents, inclusive of 5-fluorouracil (5-FU) are exemplified. Thus, there may be mentioned alkylating agents such as cyclophosphamide, melphalan, ranimustine, ifosfamide, nitrogen mustard N-oxide hydrochloride, etc.; metabolic antagonists such as 6-mercaptopurine, ribosides, enocitabine, carmofur, cytarabine, cytarabine ocfosfate, tegafur, 5-FU, doxifluuridine, doxifluridine, hydroxycarbamide, fluorouracil, methotrexate, mercaptopurine, etc.; antitumor antibiotics such as actinomycin D, aclarubicin hydrochloride, idarubicin hydrochloride, epirubicin hydrochloride, doxorubicin hydrochloride, daunorubicin hydrochloride, pirarubicin hydrochloride, bleomycin hydrochloride, zinostatin stymalamer, bleomycin sulfate, mitomycin C, neocarzinostatin, peplomycin sulfate, etc.; antitumor botanical preparations such as etoposide, irinotecan hydrochloride, docetaxel hydrate, vincristine sulfate, vindesine sulfate, vinblastine sulfate, paclitaxel, etc. and, further, aceglatone, ubenimex, cisplatin, sizofiran, sobuzoxane, krestin, toremifene citrate, medroxyprogesterone acetate, tamoxifen citrate, carboplatin, fadrozole hydrochloride hydrate, procarbazine hydrochloride, mitoxantrone hydrochloride, L-asparaginase, tretinoin, nedaplatin, picibanil, flutamide, pentostatin, porfimer sodium, lentinan, etc.

Examples of the cytokines having antitumor activity are IFN-α, IFN-β, IFN-γ, IL-1, IL-2, IL-12, TNF, TGF-β, angiostatin, thrombospondin, endostatin, etc. Examples of the antibodies or antibody fragments are antibodies or antibody fragments against factors involved in the growth and promotion of cancer, such as anti-VEGF antibody, anti-FGF antibody, anti-HGF antibody I and anti-L-8 antibody.

Thus, the angiogenesis-specific peptide of the invention can be used in producing DDS preparations, for example by coupling or modifying an active agent, such as an antineoplastic agent or a cytokine having anticancer activity, with the same and making up the product into a liposome preparation, and such preparation can be used in active targeting at cancer.

When the angiogenesis-specific peptide of the invention is to be coupled with a protein, such as a cytokine, having anticancer activity, the coupling product can be caused to be expressed as a fused protein composed of the peptide of the invention and the cytokine or the like by using the recombinant DNA technology. The production and expression of such fused protein can be realized by the conventional technology in the art. Thus, the fused protein can be prepared by the ordinary recombinant DNA technology (cf. e.g. Science, 224, 1431 (1984); Biochem. Biophys. Res. Comm., 130, 692 (1985); Proc. Natl. Acad. Sci. USA, 80, 5990 (1983)). In the production and expression of such fused protein, the method of Ohno et al. "Tanpaku Jikken Purotokoru 1 Kino Kaiseki Hen, Saibokogaku Bessatsu, Jikken Purotokoru Sirizu (Protein Experiment Protocols Book 1, Function Analyses, Supplement to Cell Engineering, Experiment Protocols Series), 1997, Shujunsha" can be referred to.

The recombinant fused protein obtained can be isolated and purified, if desired, by any of various separation procedures utilizing the physical, chemical and other properties thereof [cf. e.g. "Seikagaku Deta Bukku II (Biochemistry Data Book II)", pages 1175–1259, 1st edition, 1st printing, published Jun. 23, 1980 by Tokyo Kagaku Dojin; Biochemistry, 25 (25), 8274–8277 (1986); Eur. J. Biochem., 163, 313–321 (1987)]. Said methods specifically include, for example, ordinary reconstitution treatment, treatment with a protein precipitating agent (salting out), centrifugation, osmotic shock procedure, ultrasonic disruption, ultrafiltration, molecular sieve chromatography (gel filtration), adsorption chromatography, ion exchange chromatography, affinity chromatography, high performance liquid chromatography (HPLC), other various liquid chromatographic techniques, dialysis, and combinations thereof. Particularly preferred among the above methods is affinity chromatography using a column with the desired protein bound thereto.

When the angiogenesis-specific peptide of the invention is to be utilized as a ligand by coupling the same with a physical, chemical or biological substance, the physical, chemical or biological substance can be a drug delivery system substance such as a microdevice having cellules capable of containing the above-mentioned cancer chemotherapeutic agent (e.g. anticancer agent). Examples of such drug delivery system substance include liposomes, microcapsules having a permeable or semipermeable membrane, other microdevices having cellules and like biological substances. These substances are generally nontoxic and preferably biodegradable.

The method of coupling one of the above-mentioned various drug delivery system substances capable of containing an agent such as an anticancer agent with the peptide of the invention is well known in the relevant field of art. Specifically, the coupling is carried out by the method of Harlow or Hermanson (Harlow and Lane, Antibodies: A Laboratory Mannual, Cold Spring Harbor Laboratory Press (1988); Hermanson, Bioconjugate Techniques, Academic Press (1996)).

In the following, a liposome preparation is described in detail, as a typical example of the preparation resulting from coupling of the above-mentioned drug delivery system substance with the peptide of the invention.

The liposome preparation is obtained by causing liposomes, which comprises an acidic phospholipid as a membrane constituent or a neutral phospholipid and an acidic phospholipid as membrane constituents, to hold the peptide of the invention.

The acidic phospholipid as a membrane constituent is defined more narrowly than ordinary acidic phospholipids and specifically includes natural or synthetic phosphatidylglycerols (PGs) such as dilauroylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglycerol (DOPG), yolk phosphatidylglycerol (yolk PG) and hydrogenated yold phosphatidylglycerol as well as natural or synthetic phosphatidylinositols (PIs) such as dilauroylphosphatidylinositol (DLPI), dimyristoylphosphatidylinositol (DMPI), dipalmitoylphosphatidylinositol (DPPI), distearoylphosphatidylinositol (DSPI), dioleoylphosphatidylinositol (DOPI), soybean phosphatidylinositol (soybean PI) and hydrogenated soybean phosphatidylinositol. These may be used singly or two or more of them may be used in admixture.

Examples of the neutral phospholipid are natural or synthetic phosphatidylcholines (PCs) such as soybean phosphatidylcholine, yolk phosphatidylcholine, hydrogenated soybean phosphatidylcholine, hydrogenated yolk phosphatidylcholine, dimyristoylphosphatidylcholine (DMPC), dipalmitoylphosphatidylcholine (DPPC), dilauroylphosphatidylcholine (DLPC), distearoylphosphatidylcholine (DSPC), myristoylpalmitoylphosphatidylcholine (MPPC), palmitoylstearoylphosphatidylcholine (PSPC) and dioleoylphosphatidylcholine (DOPC), natural or synthetic phosphatidylethanolamines (PEs) such as soybean phosphatidylethanolamine, yold phosphatidylethanolamine, hydrogenated soybean phosphatidylethanolamine, hydrogenated yold phosphatidylethanolamine, dimyristoylphosphatidylethanolamine (DMPE), dipalmitoylphosphatidylethanolamine (DPPE), dilauroylphosphatidylethanolamine (DLPE), distearoylphosphatidylethanolamine (DSPE), myristoylpalmitoylphosphatidylethanolamine (MPPE), palmitoylstearoylphosphatidylethanolamine (PSPE), dioleoylphosphatidylethanolamine (DOPE), and the like. These may be used singly or two or more of them may be used in admixture.

The liposome membrane mentioned above is formed by a conventional method using the above acidic phospholipid as a single constituent or the above neutral and acidic phospholipids combinedly. Recommendably, the acidic phospholipid is used in an amount of about 0.1 to about 100 mole percent, preferably about 1 to about 90 mole percent, more preferably about 10 to about 50 mole percent, based on the liposome membrane constituents.

In preparing the above liposomes, cholesterol and/or the like may further be added. When cholesterol is added, the fluidity of phospholipids can be adjusted, whereby liposomes can be prepared more expediently. Generally, said cholesterol is added and incorporated in an amount up to the equal amount to the phospholipids, preferably half of to equal to the amount thereof.

The proportions of the active ingredient and acidic phospholipid in a liposome dispersion are recommendably such that the acidic phospholipid accounts for about 0.5 to about 100 equivalents, preferably about 1 to about 60 equivalents, more preferably about 1.5 to about 20 equivalents, relative to the active ingredient.

The amount of the peptide to be used in peptide modification according to the invention in the whole lipid, as expressed in terms of mole percent, may be several mole percent to few-score mole percent, preferably about 5 to about 10 mole percent, generally about 5 mole percent. When the peptide of the invention itself has anticancer activity, as shown later herein in Example 4, the amount may be about 5 to about 40 mole percent. For a water-soluble anticancer agent or a water soluble substance having anticancer activity, which is included in the water phase within liposomes, it is included with an efficiency of 10% to 90%. On the contrary, a liposoluble anticancer agent or a liposoluble substance having anticancer activity can be included with a high inclusion efficiency close to 100% when the desired component is included within the liposome membrane.

The method of producing the above liposomes is now described. In producing said liposomes, various known methods can be used. For example, the liposome membrane constituent is dissolved in an organic solvent such as chloroform, then the solvent is distilled off under reduced pressure to cause formation of a lipid film, an aqueous phase with the agent dissolved therein is added thereto, followed by warming to a temperature above the phase transition temperature of the lipid and further by vortex treatment, homogenization or like treatment, whereby a liposome dispersion is prepared. It is also possible to prepare a liposome dispersion by warming a powdery liposome membrane constituent to a temperature above the phase transition temperature and mixing the same with an aqueous solution of the agent with stirring. The aqueous agent solution to be added may be any one provided that the agent remains dissolved therein, and the level of addition of the aqueous agent solution can also arbitrarily increased or decreased.

If necessary, the particle size distribution of the thus-obtained liposome dispersion can be controlled by ultrafiltration, for example by using a polycarbonate membrane filter. It is also possible to concentrate the dispersion using a dialysis membrane.

In the liposome dispersion, there may be incorporated, as an additive or additives necessary from the preparation designing viewpoint, one or more of various substances such as preservatives, isotonizing agents, buffers, stabilizers, solubilizers and absorption promoters, or the liposome dispersion may be diluted with a solution containing these or water, when necessary. Specific examples of the above-mentioned additives are such preservatives as benzalkonium chloride, benzethonium chloride, chlorhexidine, parabens (e.g. methylparaben, ethylparaben), thimerosal and like preservatives effective against fungi and bacteria; isotonizing agents such as D-mannitol, D-sorbitol, D-xylitol, glycerol, glucose, mannetose, sucrose, propylene glycol, like polyhydric alcohols, sodium chloride and other electrolytes; stabilizers such as tocopherol, butylated hydroxyanisole, butylated hydroxytoluene, ethylenediaminetetraacetic acid (EDTA) and cysteine, and the like.

Specific examples of the liposome dispersion are shown later herein in Examples 5, 7 and 8.

Furthermore, the angiogenesis-specific peptide of the invention can be utilized as a cancer diagnostic agent or the like by utilizing its ability to home specifically to cancer neovascular tissues by coupling therewith a radioactive compound, fluorescent substance, enzyme, biotin, contrast agent, etc. and performing active targeting at cancer.

Further, the angiogenesis-specific peptide of the invention can be used in active targeting at cancer as a pharmaceutical composition comprising, together with an anticancer agent or a cytokine having anticancer activity, liposomes or a lipid emulsion containing said peptide in a form bound to a fatty acid (e.g. behenic acid, stearic acid, palmitic acid, myristic acid, oleic acid), an alkyl group, a cholesteryl group or the like. The details of the production of liposome preparations such as mentioned above are described, for example, in the reference by Woodle et al. (Long Circulating Liposomes: Old drugs, New therapeutics, M. C. Woodle, G. Storm, Eds., Springer-Verlag Berlin (1998)). The details of the production of pharmaaceutical compositions containing such a lipid emulsion as mentioned above together with an anticancer agent or a cytokine having anticancer activity are described in the reference by Namba et al. (Liposomal applications to cancer therapy, Y. Namba, N. Oku, J. Bioact. Compat. Polymers, 8, 158–177 (1993)).

The angiogenesis-specific peptide of the invention can also be utilized in cancer diagnosis by binding thereto one of various fatty acids, alkyl groups, cholesteryl group and so forth and making the binding product into liposomes or a lipid emulsion containing the same and further coupling therewith a radioactive compound or a contrast agent for contrasting cancer and performing active targeting at cancer using the resulting product. Thus, the peptide can serve as a cancer diagnosing agent for verifying the presence of cancer. The utilization of such diagnostic agent is advantageous particularly in that initial stage tumor and metastatic lesions, which may not be detected by other methods, can be identified. Therefore, the present invention provides a method of cancer diagnosis, in particular a diagnostic method of identifying initial stage cancer and metastatic lesions, as well.

Once the occurrence of cancer has thus been established, it becomes possible, in accordance with another aspect of the present invention, to couple the angiogenesis-specific peptide with an anticancer agent, for example a cancer chemotherapeutic agent, or with a microdevice containing a cancer chemotherapeutic agent or some other anticancer factor to thereby cause the agent to home to the cancer; thus, it becomes possible to perform the desired active targeting, namely selectively killing cancer or cancer cells while reducing the effect on normal tissues or normal cells. In this respect, the present invention provides a method for the treatment of cancer or cancer metastasis and the inhibition of cancer metastasis as well.

The angiogenesis inhibitor or cancer treatment composition of the invention is administered to patients in the form of a preparation composition containing, as the active ingredient, the angiogenesis-specific peptide or a composite thereof with another anticancer agent or the like, together with a pharmaceutically acceptable carrier.

The pharmaceutically acceptable carrier to be used can be suitably selected from among these well known in the art depending on the form of the preparation composition to be prepared. For example, when the composition is to be prepared in the form of an aqueous solution, water or a physiological buffer solution can be used as the carrier. When the composition is to be prepared in the form of an appropriate solution, glycol, glycerol, olive oil or a like injectable organic ester, for instance, may be used as the carrier.

Further, in cases where the above-mentioned composite is to be used as the active ingredient, a compound serving to stabilize or enhance the absorption of the composite, for instance, may be used. Such compounds include carbohydrates such as glucose, sucrose and dextran; antioxidants such as ascorbic acid and glutathione; chelating agents; and stabilizers or excipients such as low molecular proteins and albumin.

The content of the active ingredient in the angiogenesis inhibitor or cancer therapeutic composition (preparation) of the invention is not particularly restricted but can be selected from within a wide range. When the angiogenesis-specific peptide of the invention is used singly as the active ingredient, it is generally desirable that the content thereof in the preparation be selected within the range of about 0.00001 to about 70% by weight, preferably about 0.0001 to about 5% by weight. The dose of the above preparation is not particularly restricted, either, but can be selected within a broad range according to the desired therapeutic effect, method of administration (route of administration), treatment period, age and sex of the patient and other conditions, among others. Generally, the dose is judiciously selected within the range of about 0.01 μg to about 10 mg, preferably about 0.1 μg to about 1 mg, per kilogram of patient's body weight per day. The preparation may be administered once daily or in several divided doses per day.

The dose of the angiogenesis inhibitor or cancer treatment composition of the invention which is prepared by using the angiogenesis-specific peptide of the invention coupled to an anticancer agent and/or a cancer metastasis inhibitor can suitably be determined depending on the amount of the cancer chemotherapeutic agent (agent) required to produce the desired anticancer effect, for instance. When, for example 5-fluorouracil (5-FU), which is generally used as an anticancer active agent in the clinical application of this kind, is used, said 5-FU is administered generally at a daily dose of about 0.1 mg/kg to about 50 mg/kg. It can be readily understood by the person skilled in the art that the dose of the angiogenesis-specific peptide of the invention which is utilized in a form bound thereto is by itself evident and that such dose can be regarded as the effective dose of the peptide of the invention. Furthermore, considering that the pharmaceutical composition of the invention is characterized by the ability to specifically home to cancer neovascular tissues, it is anticipated that even when the dose of the cancer chemotherapeutic agent is considerably low as compared with the clinical dose in conventional use, remarkable effects will be produced.

As mentioned above, the angiogenesis-specific polypeptide of the invention can be bound to a radioactive compound, a contrast medium or the like for cancer imaging to give a diagnostic agent, and active targeting at cancer can be conducted using that agent. The angiogenesis-specific polypeptide of the invention can also be used in detecting the occurrence of angiogenesis in cells, tissues, organs or parts thereof as isolated from the human body. By such use, the presence of cancer in a sample isolated from the human body can be detected as a result of the fact that the neovascular tissues are ones formed by cancer. The above human sample may be a tissue section or sample obtained by biopsy, or a cell population existing in a tissue culture or adapted thereto. The human sample may be one treated by homogenization, and this is preferred.

BEST MODES FOR CARRYING OUT THE INVENTION

Figure 1:
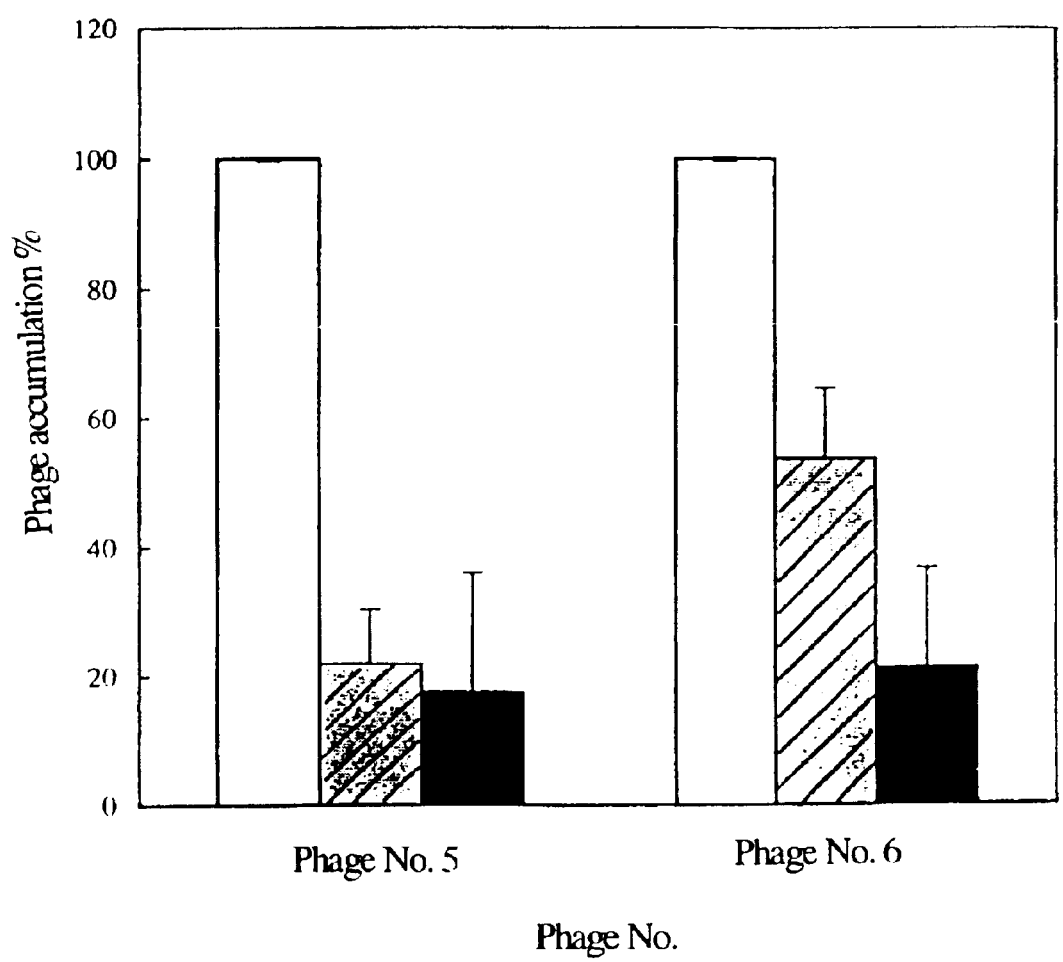
FIG. 1 is a bar graph showing the results of a competitive inhibition experiment carried out in Example 3 (3) using the phages and 8-residue synthetic peptides specified therein.

The following examples are given for illustrating the present invention in further detail. They are, however, by no means limitative of the scope of the invention.

EXAMPLE 1

Identification of Angiogenesis-specific Peptides
(1) Preparation of a Phage-displayed Library The desired phage-displayed library capable of expressing random 15-residue amino acid sequence peptides on the phage shell surface was constructed by inserting random DNAs coding for 15-residue peptides having random amino acid sequences into the phage coat protein pIII gene according to the report of Nishi, Saya et al. (Nishi T., Saya H., et al., FEBS Lett. 399, 237–240 (1996)).

Scott et al reported the characteristic features of the phage-displayed library constructed in the above manner (Scott, J. K. and Smith, G. P., Science, 249, 386–390 (1990)).
(2) Angiogenesis The chamber ring method (Folkman, J., et al., J. Exp. Med., 133, 275–288 (1971)) was employed for inducing in vivo tumor neovascular tissues to serve as targets of angiogenesis-specific peptide-expressing phages.

The chamber ring method is one of techniques established for inducing tumor neovascular tissues in vivo. It comprises enclosing tumor cells in a ring and implanting the same subcutaneously into an animal to thereby induce dermal neovascular tissues. The filters of the ring have properties such that they do not allow the permeation of cells but allow the permeation of humoral factors alone. Therefore, by the technique, it is possible to induce angiogenesis without causing cancer metastasis to tissues of the animal and without causing cancer cells to be damaged by immunocytes.

The technique is mentioned below in detail. First, 0.18 ml of a suspension of B16BL6 melanoma cells (obtained from Dr. G. L. Nicolson (Institute for Molecular Medicine Irvine, Calif.; cf. e.g. Cancer Res., 57, 3612–3619 (1997); FEBS Lett., 427, 286–290 (1998)) ($1 \times 10^7$ cells/0.18 ml) was injected into each ring (outside diameter 14 mm, inside diameter 10 mm, height 2 mm, 0.2-ml Millipore ring PR0001401 for carp cultivation, product of Millipore) through the inlet opening using a syringe and the opening was plugged with a nylon rod (product of Millipore). Then, the ring was dorsally implanted into a 5-week-old C57BL/6 male mouse to thereby cause angiogenesis in the mouse dorsal skin.

(3) Screening for Angiogenesis-specific Peptide-displaying Phages (Biopanning)

Five days after chamber ring implantation, each mouse was anesthesized with nembutal (intraperitoneal administration of 0.2 ml), and 0.2 ml of the random peptide-displaying phage ($1 \times 10^{11}$ colony forming units) obtained as mentioned above under (1) was administered into the tail vein. Four minutes after administration, the mouse was frozen in liquid nitrogen. The frozen mouse was thawed using a drier and the skin showing neovascularization was dissected and weighed.

The skin obtained was then minced, 1 ml of Dulbecco's modified Eagle culture solution (A) (product of Nissui Pharmaceutical, catalog No.: Code 05915) containing 1 mM phenylmethylsulfonyl fluoride (protease inhibitor; product of Sigma) was added thereto, and the mixture was homogenized on ice. Then, the homogenate was transferred to an Eppendorf tube and washed with three ice-cooled portions of the above culture solution (A) containing 1% bovine serum albumin (product of Intergene) (BSA 0.1 g +100 mM PI, 100 $\mu$l+DMEM 10 ml). The washing was carried out at 12,000 revolutions/minute using a centrifuge. Thereafter, the supernatant was removed and the phages recovered from the neovascular tissue were infected to *Escherichia coli* K91KAN (kanamycin-resistant strain; gift from Dr. Hideyuki Saya, Kumamoto University Chair of Tumor Medicine). After 60 minutes of standing, to the infected strains were added 10 ml of NZY medium [prepared by dissolving 10 g of NZ amine A (product of Wako Pure Chemical; Code: 541-00241), 5 g of beer yeast extract (trademark: Ebios, product of Asahi Brewery) and 5 g of NaCl in 1 liter of purified water, adding 1 ml of 5 N NaOH to adjust to pH 7.5 and sterilizing by autoclaving and stored at room temperature) containing 0.2 $\mu$g/ml of tetracycline and the mixture was incubated at 180 to 200 revolutions/minute for 60 minutes at 37° C.

Then, one colony of streak-cultured *Escherichia coli* K91KAN was scratched off, suspended in 5 ml of NZY medium containing kanamycin (product of Wako Pure Chemical, final concentration 100 $\mu$g/ml) and incubated overnight at 37° C. and at 180 to 200 revolutions/minute. Further, 100 $\mu$l of the culture fluid was suspended in 10 ml of kanamycin-containing NZY medium and incubated at 180 to 200 revolutions/minute for 4 hours at 37° C. After 4 hours of cultivation, it was confirmed that a sample prepared by 10-fold dilution of the culture fluid showed an absorbance of 0.1 to 0.2 at 600 nm (the number of cells being $5 \times 10^9$ cells/ml). After 30 minutes of standing, phages were separated and purified and used for the second and subsequent biopanning procedures.

After 5 repetitions of the above procedure, the desired phages expressing a peptide accumulating in neovascular tissues were obtained. The results of the above biopanning procedures are shown in Table 1.

TABLE 1

| Biopanning | Phage recovery rate | Phage concentration rate |
|---|---|---|
| 1st | $2.11 \times 10^{-6}$ | 1.0-fold |
| 2nd | $2.74 \times 10^{-6}$ | 1.3-fold |
| 3rd | $6.73 \times 10^{-6}$ | 3.2-fold |
| 4th | $5.77 \times 10^{-5}$ | 27.3-fold |
| 5th | $2.09 \times 10^{-3}$ | 990.5-fold |

Table 1 shows the phage recovery rates obtained by the 1st to 5th biopanning. As shown in the table, it is seen that the phage recovery rate given in terms of percentage ratio of the number of phages which accumulated at the neovascular tissue site to the number of phages administered into the tail vein increased with the increase in the number of biopanning procedures. It was confirmed that the phages expressing a peptide specifically binding to angiogenic vessel endothelial cells had been recovered.

(4) Sequencing of Angiogenesis-specific Peptides

For 15 phages among the phages obtained as mentioned above under (3), the peptides expressed were sequenced as follows.

Thus, 50 colonies were randomly picked up from each plate obtained after titer measurement following the 4th biopanning and reinoculated into a fresh NZY plate and, after overnight incubation at 37° C., the plate was stores at 4° C. as a master plate.

Each colony on the master plate was suspended in 20 ml of NZY medium (containing 20 $\mu$g/ml of tetracycline) placed in a 50-ml centrifuge tube and shake-cultured overnight at 37° C. and at 200 revolutions/minute.

Then, the culture was centrifuged at 3,000 revolutions/minute for 10 minutes, and the supernatant was transferred to an Oak Ridge centrifuge tube and centrifuged at 12,000 revolutions/minute for 10 minutes to thereby eliminate *Escherichia coli*. Further, the supernatant was transferred to an Oak Ridge centrifuge tube and after addition of 3 ml of polyethylene glycol (PEG 6000; product of Nakalai Tesque)/NaCl and thorough stirring, the mixture was allowed to stand at 4° C. for 4 hours, followed by 10 minutes of centrifugation at 12,000 revolutions/minute to cause phages to precipitate. After removal of the supernatant, the phage sediment was suspended in 1 ml of TBS (Tris-buffered saline). The suspension was transferred to a 1.5-ml Eppendorf tube, followed by 10 minutes of centrifugation at 15,000 revolutions/minute. The insoluble matter was removed and the supernatant was transferred to another Eppendorf tube. To the supernatant 150 $\mu$l of polyethylene glycol/NaCl was added and after thorough stirring, the mixture was allowed to stand at 4° C. for 1 hour. Then, the phage was reprecipitated by 10 minutes of centrifugation at 15,000 revolutions/minute. After the removal of the supernatant, the phage precipitate was resuspended in 200 $\mu$l of TBS. The insoluble matter was precipitated by 10 minutes of centrifugation at 15,000 revolutions/minute, the sediment was transferred to a 0.5-ml Eppendorf tube and the phage clone was stored at 4° C.

For extracting DNA from the phage clone obtained in the above manner, 100 $\mu$l of TBS and 200 $\mu$l of TE-saturated phenol (product of Nippon Gene) were added to 100 $\mu$l of the phage clone placed in a 1.5-ml Eppendorf tube and, after 10 minutes of vigorous stirring, the mixture was centrifuged at 15,000 revolutions/minute for 10 minutes. Then, 200 $\mu$l of TE-saturated phenol and 200 $\mu$l of chloroform were added to 200 $\mu$l of the supernatant (aqueous phase) and, after 10 minutes of vigorous stirring in the same manner as above, the mixture was centrifuged at 15,000 revolutions/minute for 10 minutes. Further, 250 μl of TE, 40 μl of 3 M sodium acetate, 1 μl of 20 mg/ml glycogen (product of Boehringer Mannheim) and 1 ml of ethanol were added to 150 μl of the supernatant (aqueous phase), and the mixture was allowed to stand in a 1.5-ml Eppendorf tube at −20° C. for 1 hour, followed by centrifuged at 15,000 revolutions/minute for 10 minutes. The supernatant was removed, 1 ml of 80% ethanol (−20° C.) was gently added to the precipitate and the mixture was centrifuged at 15,000 revolutions/minute for 10 minutes to thereby remove the remaining salt. After removal of the supernatant, the water in the tube was evaporated, the precipitate DNA was dissolved in 10 μl of sterilized distilled water and the solution was stored at 4° C. The respective phage DNAs thus obtained were used to peptide sequencing.

The sequencing of the peptide encoded by each phage DNA was carried out by the dideoxy method (Proc. Natl. Acad. Sci. USA, 74, 5463–5467 (1977)) using Amersham's THERMO sequencing kit (Amersham Life Science, Code: US79765, Lot No.: 201503) and following the user's manual attached to the equipment. The DNA elongation reaction was carried out in 30 cycles, each cycle comprising 96° C.×30 seconds, 45° C.×15 seconds and 60° C.×4 minutes, and the DNA sequencing was carried out using an ABI DNA sequencer (ABI PRISMTM 377 DNA sequencer).

The thus-determined amino acid sequences of the angiogenesis-specific peptides are shown in Table 2 according to the one-letter abbrevation.

TABLE 2

| Phage No. | Peptide sequence |
| --- | --- |
| SEQ ID NO: 1 | PRPGAPLAGSWPGTS (5 phages) |
| SEQ ID NO: 2 | AXEWLDALFVRHVDR |
| SEQ ID NO: 3 | AAEWLDAFFVRHVDR |
| SEQ ID NO: 4 | APCCSHLDASPFQRP |
| SEQ ID NO: 5 | DRWRPALPVVLFPLH |
| SEQ ID NO: 6 | ASSSYPLIHWRPWAR |
| SEQ ID NO: 7 | RASDVGSDVVPRYPF |
| SEQ ID NO: 8 | XFARAPVEHHDVVGL |
| SEQ ID NO: 9 | GDVWLFLTSTSHFAR |
| SEQ ID NO: 10 | PAQSNFVTWGYNVAV |
| SEQ ID NO: 11 | EGCSVSSVGALCTHV |

As shown above in Table 2, five phages among 15 phages expressed the peptide sequence shown for phage No. 1. The peptide sequences shown for phages Nos. 2 to 11 were each respectively expressed by one phage.

(5) Test for Affinity of Angiogenesis-specific Peptide-expressing Phages (Affinity Test 1)

Tumor-bearing mice were prepared by implanting B16BL6 melanoma cells (1×10$^6$ cells) into the left flank of five-week-old C57BL/6 male mice. Ten days after tumor implantation (when the solid tumor had a diameter of about 1 cm), the tumor-bearing mice were anestheized with nembutal (0.2 ml administered intraperitoneally) in a similar manner as described above under (3) and 0.2 ml of one of the phages expressing the sequenced peptides Nos. 1 to 11 and of the phage before administration into the tail vein were administered, respectively, into the tail vein (1×10$^{11}$ colony forming units). Four minutes after administration, the mice were frozen in liquid nitrogen. The frozen mice were thawed using a drier and the tumor sites were dissected and weighed.

Each tumor was minced, and the phage was infected VII into Escherichia coli in a similar manner as described above under (3) and then incubated. Thereafter, the colony forming units for each phage accumulated in the tumor tissue were counted in the similar manner.

The results (recovery percentages) obtained are shown in Table 3 in terms of the percentage ratio of the number of phages accumulated to the number of phages administered into the tail vein per 100 mg of the tumor tissue. The affinity of each angiogenesis-specific peptide-displaying phage for tumor tissue is also shown in Table 3 in terms of the relative binding of each peptide-expressing phage with the phage recovery rate before sorting out being taken as 1.

TABLE 3

| Phage No. | Recovery rate (% 100 mg tissue) | Affinity |
| --- | --- | --- |
| No. 5 | 2.90 × 10$^{-2}$ | 64.1 |
| No. 6 | 2.42 × 10$^{-2}$ | 53.5 |
| No. 1 | 1.12 × 10$^{-2}$ | 24.8 |
| No. 2 | 6.00 × 10$^{-3}$ | 13.3 |
| No. 3 | 3.61 × 10$^{-3}$ | 7.99 |
| No. 9 | 2.37 × 10$^{-3}$ | 5.24 |
| No. 11 | 2.19 × 10$^{-3}$ | 4.85 |
| No. 4 | 1.64 × 10$^{-3}$ | 3.62 |
| No. 10 | 1.28 × 10$^{-3}$ | 2.83 |
| No. 7 | 6.69 × 10$^{-4}$ | 1.48 |
| No. 8 | 4.87 × 10$^{-4}$ | 1.08 |
| Phage before sorting out | 4.52 × 10$^{-4}$ | 1.0 |

From the above table, it is seen that the phages Nos. 5, 6, 1, 2 and 3 show high affinity for tumor in that order.

(6) Test for Affinity of Angiogenesis-specific Peptide-expressing Phages (Affinity Test 2)

Whether the peptide-expressing phages sorted out as mentioned above under (5) show specific adhesion to neovascular tissues in a different strain of mice and for a different tumor strain as well was tested as followed.

Thus, tumor-bearing mice were prepared by implanting Meth A sarcoma cells (1×10$^6$ cells) into the left flank of five-week-old BALB/c male mice. Thereafter, a similar test as described above under (5) was carried out.

The results obtained are shown below in Table 4 in the same manner as in Table 3.

TABLE 4

| Phage No. | Recovery rate (% 100 mg tissue) | Affinity |
| --- | --- | --- |
| No. 1 | 5.36 × 10$^{-3}$ | 45.0 |
| No. 5 | 4.29 × 10$^{-3}$ | 36.1 |
| No. 6 | 3.49 × 10$^{-3}$ | 29.3 |
| Phage before sorting out | 1.19 × 10$^{-4}$ | 1.0 |

From the above table, it was revealed that the phaqes Nos. 1, 5 and 6 have high affinity for tumor in that order.

It was, thus, found that phages No. 1, No. 5 and No. 6 show high affinity for such different types of tumors involving neovascularization as above, although some minor differences are noted in the degree of affinity.

EXAMPLE 2

Solid Phase Synthesis of Peptides of the Invention

Each peptide was prepared by the solid phase synthesis according to the Fmoc/NMP, HOBt method [Fmoc: g-fluorenylmethoxycarbonyl, NMP: N-methylpyrrolidone, HOBt: 1-hydroxybenzotriazole] using an automatic peptide synthesizer (ACT357, product of Advanced ChemTech) and the program of the manufacturer, as follows.

Thus, the C-terminal free (OH) peptides were first prepared. These were prepared according to the amino acid sequences shown in SEQ ID NO:1 to 12 by repeating the elongation reaction according to the respective programs of synthesis starting with 0.25 mmol of the Fmoc-amino acid- Alko resin corresponding to the C-terminal amino acid of each peptide and subjecting to reaction the Fmoc-amino acids corresponding to the second (from the C terminus) and subsequent amino acids one by one.

The C-terminal amide form of peptide was prepared by condensing reaction of 0.25 mmol of the Fmoc-NH-SAL resin with Fmoc-amino acid corresponding to the C terminal amino acid, followed by subjecting to the condensing reaction with Fmoc-amino acids corresponding to the second (from the C terminus) and subsequent amino acids one by one.

After completion of each reaction process, the N-terminal Fmoc group was eliminated according to the program.

Each peptide resin thus obtained was recovered in a polypropylene minicolumn (product of Assist), washed with methanol and dried under vacuum and the peptide was excised from the resin by the procedure mentioned below, followed by the side chain deprotection reaction. Thus, 2 ml of Reagent K (82.5% TFA, 5% phenol, 5% $H_2O$, 5% thioanisole, 2.5% ethanedithiol) was added to each resin and the reaction was carried out in a minicolumn for 60 minutes.

Then, the reaction was terminated and at the same time the peptide was precipitated, by adding the reaction mixture dropwise into 8 ml of cold diethyl ether. Further, the minicolumn was washed with 2 ml of TFA, 5 ml of cold diethyl ether was added, the mixture was centrifuged, the precipitate was washed with four 10-ml portions of diethyl ether, and the peptide was then solubilized with about 5 ml of 50% acetonitrile and lyophilized. The solubilization. and lyophilization procedures were further repeated twice, whereby the desired crude lyophilizate was obtained.

The crude lyophilizate was fractionated by reversed phase high performance liquid chromatography (HPLC) using an Octadecyl column (diameter 20×250 mm, product of YMC), and the desired peptide was isolated.

The resins and amino acid derivatives used in the above processes were products of Watanabe Kagaku Kogyo.

Each peptide thus isolated was identified by amino acid sequence analysis and molecular weight determination by mass spectrometry.

EXAMPLE 3

Competitive Inhibition Experiment Using Synthetic Peptides (1) Peptide Synthesis In view of the test results obtained above in Example 1, attention was paid to the common sequence occurring in the three peptides showing high affinity for angiogenic sites and tumor tissues, the peptides shown in SEQ ID NO:13 to 16 were further synthesized by the solid phase peptide synthesis method shown in Example 2 in addition to the peptides shown in SEQ ID NO:1, 5 and 6, which contain the structure XRP. In the following examples, the peptides of the invention used were the peptides thus obtained and having the C-terminal amide structure, unless otherwise specified.

(2) Competitive Inhibition Experiment Using the Respective Phages and Synthetic 15-residue Peptides The synthetic peptides having the amino acid sequences shown in SEQ ID NO:1, 5 and 6 were respectively administered simultaneously with the phages No. 1, No. 5 and No. 6 in a similar manner as in Example 1 (5). Each peptide was synthesized as in Example 2.

Thus, 10 days after implantation of B16BL6 melanoma ($1\times10^6$ cells) into five-week-old C57BL/6 mice (obtained from Japan SLC), a mixed solution (0.2 ml) of 0.25 μmol of one of the above synthetic peptides and the respective phage ($1\times10^8$ colony forming units) was administered into the tail vein of each tumor-bearing mouse under anesthesia, and the colony forming units of the phage accumulated in the tumor tissue were counted in a similar manner as mentioned above.

In a control group, synthetic peptide-free phage solutions ($1\times10^8$ colony forming units) were administered.

Phages accumulated in neovascular tissues in tumor tissues were counted through colony formation, and each synthetic peptide was evaluated for its inhibitory effect on phage accumulation using, as a reference value, the ratio of accumulation of the peptide-expressing phage in tumor without simultaneous administration of the synthetic peptide.

The results obtained are shown in Table 5.

TABLE 5

| Phage No. | Synthetic peptide | % Dose/100 mg tissue | Accumulation inhibition % |
|---|---|---|---|
| No. 1 | SEQ ID NO: 1 | $5.95 \times 10^{-3}$ | 55 |
|  | SEQ ID NO: 5 | $6.36 \times 10^{-3}$ | 52 |
|  | SEQ ID NO: 6 | $5.92 \times 10^{-3}$ | 55 |
|  | (No administration) | $1.33 \times 10^{-2}$ | — |
| No. 5 | SEQ ID NO: 1 | $1.35 \times 10^{-2}$ | 9 |
|  | SEQ ID NO: 5 | $5.08 \times 10^{-3}$ | 66 |
|  | SEQ ID NO: 6 | $3.61 \times 10^{-3}$ | 76 |
|  | (No administration) | $1.48 \times 10^{-2}$ | — |
| No. 6 | SEQ ID NO: 1 | $1.14 \times 10^{-2}$ | — |
|  | SEQ ID NO: 5 | $6.60 \times 10^{-3}$ | 43 |
|  | SEQ ID NO: 6 | $6.43 \times 10^{-3}$ | 44 |
|  | (No administration) | $1.15 \times 10^{-2}$ | — |

From the above table, the followings were revealed. Thus, the synthetic peptides (SEQ ID NO:5 and 6) having the common amino acid sequence (WRP) showed crosswise inhibitory activity against the phages Nos. 5 and 6, suggesting that the above common sequence WRP is important for the affinity for angiogenic sites.

On the other hand, the accumulation of the No. 1 phage in tumor was inhibited to almost the same extent by all the synthetic peptides used.

(3) Competitive Inhibition Experiment Using the Respective Phages and Synthetic 8-Residue or 5-Residue Peptides Using a similar method as described above under (2) and using the four short-chain peptides (SEQ ID NO:13 to 16) obtained as mentioned above under (2) in lieu of the synthetic peptides (SEQ ID NO:5 and 6), the synthetic peptides and the respective phages were administered and colony forming units for the phages accumulated in the tumor tissue were counted, and the short-chain synthetic peptides were evaluated for their inhibitory effect on phage accumulation. In a control group,synthetic peptide-free phage solutions ($1\times10^8$ colony forming units) were administered.

Figure 2:
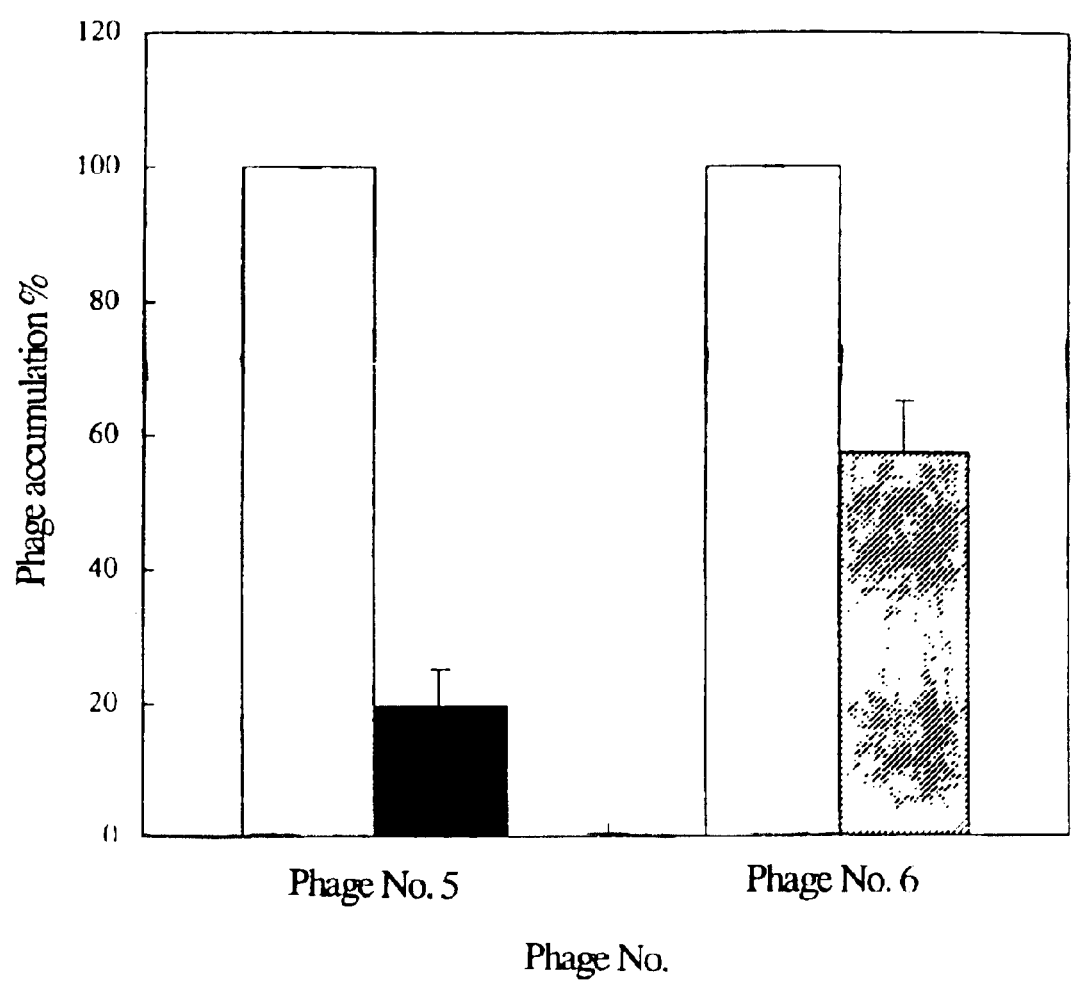
FIG. 2 is a bar graph showing the results of a competitive inhibition experiment carried out in Example 3 (3) using the phages and 5-residue synthetic peptides specified therein.

The results are shown in FIG. 1 and FIG. 2.

In each figure, the ordinate denotes the phase accumulation percentage (%) and the abscissa denotes the phage number. In FIG. 1, the open bar is for the group (control group) given the phage alone without administration of any synthetic peptide, the shaded bar is for the group given the short-chain synthetic peptide shown in SEQ ID NO:13 and the closed bar is for the group given the short-chain synthetic peptide shown in SEQ ID NO:14.

As shown in FIG. 1, the 8-residue short-chain synthetic peptides (SEQ ID NO:13 and 14) containing the sequence WRP common to the synthetic peptides having the amino acid sequences shown in SEQ ID NO:5 and 6 inhibited the accumulation of the phages expressing the 15-residue peptides respectively corresponding thereto. They were higher in inhibitory activity than the 15-residue synthetic peptides. Both showed cross reactivity, suggesting the importance of the common sequence WRP and it is considered possible to further curtail the chain.

In FIG. 2, the open bar is for the group (control group) given the phage alone without administration of any synthetic peptide, the closed bar is for the group given the short-chain peptide shown in SEQ ID NO:15 (where phage No. 5 was used) and the shaded bar is for the group given the short-chain peptide shown in SEQ ID NO:16 (where phage No. 6 was used).

From FIG. 2, it is evident that the peptides (5 residues) having a further curtailed chain as shown in SEQ ID NO:15 and 16, which have the common sequence WRP, inhibit likewise the accumulation in tumor of the phages respectively expressing the corresponding 15-residue peptides.

EXAMPLE 4

Tumor Growth Inhibiting Activity 1
(1) Synthesis of Dendrimer Peptides

In examining peptides for tumor growth inhibiting activity, an examination was carried out using multiple antigen peptides (MAPs), namely dendrimer peptides, expected to provide the peptide to be administered with increased stability and enhanced activity. The dendrimer peptides was prepared by a similar solid phase method as shown in Example 2 using an Fmoc-MAP-Alko resin. The resin used for the synthesis of dendrimer peptides was an $Fmoc_8$-$Lys_4$-$Lys_2$-Lys-βAla-Alko resin (Fmoc-MAP-Alko resin, product of Watanabe Kagaku Kogyo).

The structures of the dendrimers obtained by using the synthetic peptides (obtained in Example 2) shown in SEQ ID NO:1, 5 and 6, respectively, have the following structures when expressed according to the one letter abbreviation.
<Dendrimer Peptides>
(1) Dendrimer peptide derived from the peptide shown in SEQ ID NO;1:

(PRPGAPLAGSWPGTS)$_8$-$Lys_4$-$Lys_2$-Lys-βAla
(2) Dendrimer peptide derived from the peptide shown in SEQ ID NO:5:

(DRWRPALPVVLFPLH)$_8$-$Lys_4$-$Lys_2$-Lys-βAla
(3) Dendrimer peptide derived from the peptide shown in SEQ ID NO:6:

(ASSSYPLIHWRPWAR)$_8$-$LYs_4$-$Lys_2$-Lys-βAla
(2) Angiogenesis inhibiting effects of dendrimer peptides Solid tumor-bearing mice were prepared by subcutaneously administering 0.2 ml of Meth A sarcoma cells ($5×10^6$ cells/ml) into the left flank of five-week-old BALB/c male mice (Japan SLC). After 6 to 10 days from sarcoma implantation, when the diameter of the post-implantation tumor in tumor-bearing mice arrived at 4 mm was taken as day 1 and, on days 1 to 11, distilled water (D.W.) as a control or 20 mg/kg/day of each of the above dendrimers (1) to (3) was subcutaneously administered for 11 consecutive days (4 mice were used in each group).

The antitumor effect of each dendrimer peptide was evaluated 6 days after implantation and thereafter by examining the tumor growth, the body weight change and the survival time (days) as an indicator of side effect. At the same time, the minor axis and major axis of each tumor were measured and the tumor volume was calculated according to the formula shown below. The tumor volume calculated by the formula shows very high correlation with the tumor weight found by excising the tumor and weighing the same ($r^2$=0.980).

Tumor volume=0.4×a×$b^2$ (a: major axis, b: minor axis)

Figure 3:
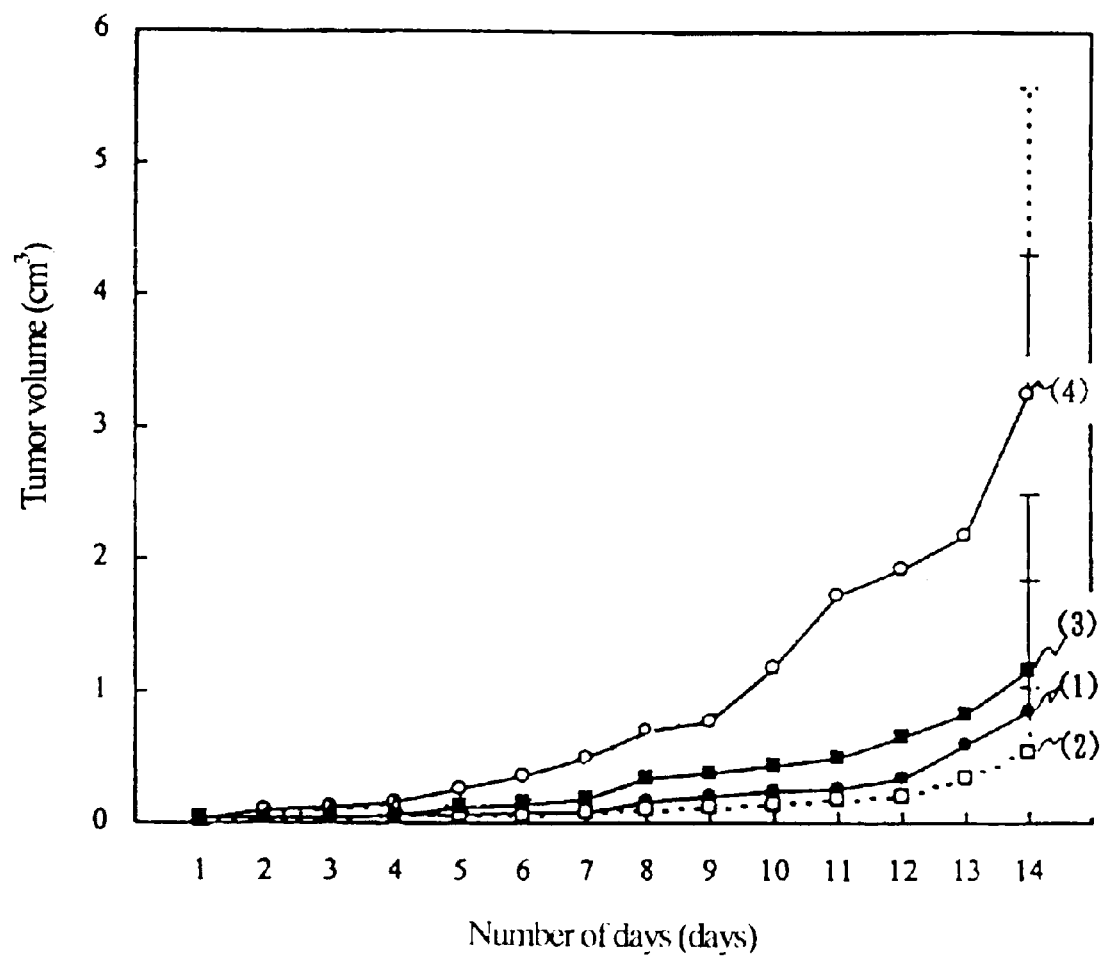
FIG. 3 is a graphic representation of the angiogenesis inhibiting effects of the dendrimer peptides shown in Example 4 (2).

The results obtained are shown in FIG. 3.

In FIG. 3, the ordinate denotes the tumor volume ($cm^3$) and the abscissa denotes the number of days (days) and, in the figure, the curve (1) is for the group given the dendrimer (1) mentioned above, the curve (2) is for the group given the dendrimer (2) mentioned above, the curve (3) is for the group given the dendrimer (3) mentioned above, and the curve (4) is for the group given distilled water.

From FIG. 3, it was revealed that, as compared with the administration of distilled water, the administration of the dendrimer peptides derived from the peptides having the amino acid sequences shown in SEQ ID NO: 1, 5 and 6 produced marked tumor growth inhibiting effects. From the result, it was confirmed that the peptides having the amino acid sequences shown in SEQ ID NO:1, 5 and 6 produce, in the form of dendrimers, excellent tumor growth inhibiting effects.

EXAMPLE 5

In Vivo Distribution of Peptide-modified Liposomes

Liposomes modified with the angiogenesis-specific peptides of the invention, in particular the peptides containing the sequence WRP or the sequence PRP, if in vivo distribution thereof is specific to neovascular tissues in tumor and/or sites surrounding tumor, can be made into DDS preparations allowing active targeting at tumor/cancer in the form of pharmaceutical preparations containing a desired anticancer agent or a cytokine having anticancer activity.

Therefore, in this example, stearic acid was bound to the N terminus of the 5-residue peptides containing the sequence WRP or the sequence PRP and liposomes were prepared using the products, and an investigation was made as to whether the liposomes prepared were accumulated in the target tumor.
(1) Preparation of Liposome Dispersions For preparing liposome dispersions, stearic acid derivatives of the angiogenesis-specific peptides of the invention (partial peptides; SEQ ID NO:15: partial peptide of SEQ ID NO:5, SEQ ID NO:16: partial peptide of SEQ ID NO:6 and SEQ ID NO:17: partial peptide of SEQ ID NO:1 with Ala added to the N terminus thereof) were prepared by the method of Example 2.

Then, chloroform solutions containing lipid DSPC (distearoylphosphatidylcholine; product of Nippon Seika), cholesterol (product of Sigma) and one of the above three angiogenesis-specific peptides (stearic acid derivatives of partial peptides) of the invention in the mole ratio of 10:5:4 were prepared.

Thus, chloroform solutions containing the above ingredients in the mole ratio of 10:5:4 were prepared by admixing 75 μl of 100 mM DSPC, 37.5 μl of cholesterol, 30 μl of each peptide of the invention and [oleate-1-$^{14}$C]-labeled cholesterol oleate (555 KBq; product of Amersham) together. Then, each solution prepared in the above manner was placed in a round-bottom flask and a thin lipid film was prepared by removing the chloroform under reduced pressure using a rotary evaporator. Further, the chloroform was completely removed under reduced pressure and the thin film was dried. After 60 minutes of drying under vacuum, the film was hydrated with 0.3 M glucose (DSPC concentration: 5.0 mM).

Usually, in lieu of 0.3 M glucose, an anticancer substance or an ingredient having antitumor activity, such as 5-FU or doxorubicin, isotonized with glycerol or the like is used as an active ingredient. Also, when the ingredient having antitumor activity is a plasmid containing a specific DNA fragment or a protein, liposomes are prepared by adding Dulbecco's phosphate-buffered physiological saline (PBS)-Mg or Ca-containing solution or the like or, after liposome preparation, an anticancer agent such as adriamycin is caused to be included in liposomes by the remote loading method. However, since the angiogenesis-specific peptides of the invention have themselves antitumor activity as shown in Example 3, neither anticancer substance nor ingredient having antitumor activity was added in the subsequent preparation steps, as follows.

The solution prepared in the above manner was subjected to three repetitions of freezing and thawing by warming at 70° C. and then sonicated with stirring for 10 minutes using a warm bath type sonicator (trademark: ULTRASONIK 250; product of Labosco). Then, using an extruder (product of Lipex), the solution was passed through a polycarbonate membrane (Nucleopore polycarbonate; product of Coaster) having 100-nm pores three times to give the desired liposomes (dispersion) containing the molecule resulting from coupling of stearic acid to the N terminus of the angiogenesis-specific peptide (partial peptide) of the invention. In this product, the partial peptide is in a form modifying the liposome surface.

The resulting liposome dispersions contain DSPC, cholesterol and one of the angiogenesis-specific peptides of the invention (three partial peptides; SEQ ID NO:15: RWRPA, SEQ ID NO:16: HWRPW and SEQ ID NO:17: APRPG) in amounts of 7.5 μmol, 3.75 μmol and 3 μmol, respectively, in 1.5 ml.

(2) In Vivo Distribution of Liposomes in Tumor-bearing Mice

Solid tumor was formed by subcutaneously implanting Meth A sarcoma cells ($1 \times 10^6$ cells/0.2 ml) into the flank of five-week-old BALB/c mice. After 10 days, 0.2 ml/mouse of each of the three liposome dispersions prepared as mentioned above under (1) was administered into the tail vein of the tumor-bearing mice under anesthesia, and examined for the in vivo distribution in the tumor tissue and various organs of the mice. As a control, a synthetic to peptide-free liposome dispersion was administered. Two or three tumor-bearing mice were used per group.

Three hours after the administration of the test solution, the tumor-bearing mice were exsanguinated, then sacrificed by cervical dislocation and subjected to autopsy to collect the blood, tumor tissue and organs (heart, lung, liver, spleen and kidney). Each organ was weighed. The blood was transferred to an Eppendorf tube and centrifuged at 3,000 rpm for 5 minutes and 50 μl of the serum obtained was stored in a vial. Each organ was cut to a size of about 100 mg, placed in a vial and, after organ weighing, stored (each organ sample was collected from two sites). Each organ sample in the vial was then minced, 1 ml of a tissue lyzing solution (Solvable; product of NEN Research Productions) was added, and the mixture was allowed to stand overnight in an incubator (Personal DX; product of Titertek) at 50° C. On the next day, 0.5 ml of isopropanol (product of Wako Pure Chemical) was added as an antifoaming agent and 0.5 ml of hydrogen peroxide was then added as a decoloring agent, and the mixture was allowed to stand for several hours.

Thereafter, 10 ml of a scintillator (HionicFlow; product of Packard Bioscience) was added, and the vial was shaken well and then further allowed to stand overnight. The test samples thus prepared were measured for in vivo distribution of the peptide-modified liposomes in the respective organs, inclusive of the tumor tissue using a liquid scintillation counter (LSC-3100; product of Aloka). For each measurement, two tubes each of the blank and a mixture prepared by adding 10 ml of the scintillator ((HionicFlow; product of Packard Bioscience) to 50 μl of liposomes were prepared.

Figure 4:
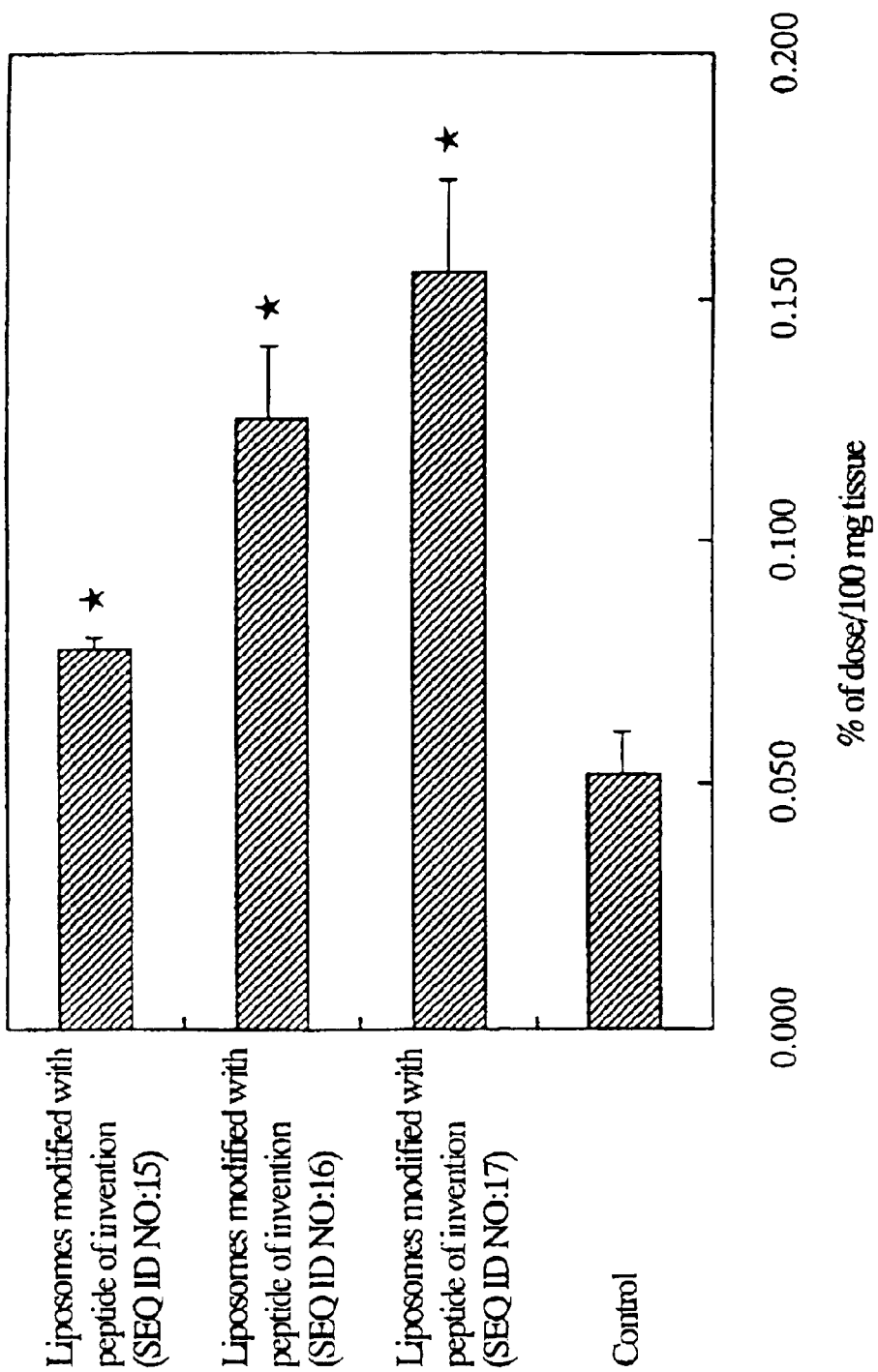
FIG. 4 is a graphic representation of the in vivo distributions of the liposome solutions in tumor-bearing mice as shown in Example 5 (2).

The results thus obtained are shown in FIG. 4. In the figure, the numerical values indicate the rates of recovery (% of the dose) of the peptide-modified liposomes administered in 100 mg of the tumor tissue.

As is evident from the figure, the liposomes modified with the angiogenesis-specific peptides of the invention (partial peptides, SEQ ID NO:15: partial peptide of SEQ ID NO:5; RWRPA, SEQ ID NO:16: partial peptide of SEQ ID NO:6; HWRPW and SEQ ID NO:17: partial peptide of SEQ ID NO:1; APRPG) all showed significantly higher levels of distribution in tumor as compared with the control (in the figure, the mark ★ indicates that the difference is significant as compared with the control ($p<0.05$)).

It was further revealed that the liposomes modified with these angiogenesis-specific peptides of the invention show a tendency toward increased retention in blood as compared with the liposomes not modified with such peptides (control, no peptide added).

As for the distribution of each of the above peptides in other organs, the tendency shown was as a whole similar to that in the control, with a tendency toward slight decrease in pancreas, lung and liver. This tendency was remarkable particularly with the peptide shown in SEQ ID NO:17.

EXAMPLE 6

Tumor Growth Inhibiting Activity 2

(1) Examination of Dendrimers of the Peptide Shown in SEQ ID NO:1 for Dose-dependent Tumor Growth Inhibiting Activity Doses of 10 mg/kg×twice/day and 20 mg/kg×twice/day of the dendrimer peptide derived from the peptide of SEQ ID NO:1 as synthesized in Example 4 (1) and a dose of 20 mg/kg×twice/day of a dendrimer peptide (SEQ ID NO:18) derived from a peptide resulting from replacement of an arbitrary sequence for the sequence shown in SEQ ID NO:1, and distilled water (DW) as a control were subcutaneously administered to mice on days 1 to 10 after tumor cell implantation according to the method of Example 4 (2), and the tumor growth inhibiting activities were examined. Four to six mice per group were subjected to the experiment. The results obtained are shown in FIG. 5 in the same manner as in FIG. 3 (ordinate: tumor volume ($cm^3$), abscissa: days after tumor cell implantation (days)).

In the figure, open circles are for the group given 10 mg/kg twice/day of the dendrimer peptide, closed circles are for the group given 20 mg/kg×twice/day of the dendrimer peptide, open squares are for the group given 20 mg/kg× twice/day of the dendrimer peptide derived from a peptide resulting from arbitrary sequence replacement, and closed squares are for the group given distilled water.

Figure 5:
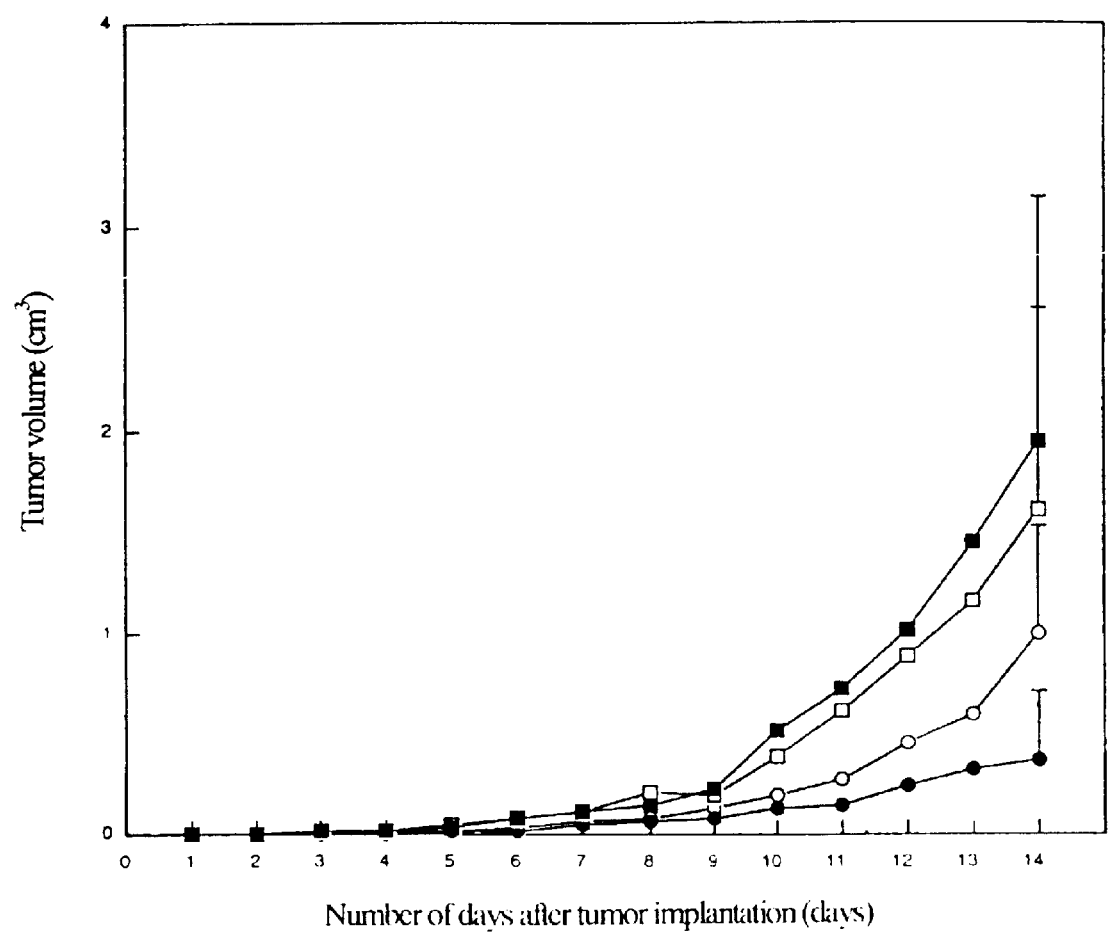
FIG. 5 is a graphic representation of the tumor growth inhibiting effects of the dendrimer peptides shown in Example 6 (1).

From FIG. 5, it is apparent that, as compared with the group given the dendrimer peptide derived from a peptide resulting from arbitrary sequence replacement for the sequence shown in SEQ ID NO:1 and the group given distilled water, the groups given the dendrimer peptide containing the sequence shown in SEQ ID No:1 shows a dose-dependent tumor growth inhibiting activity.

(2) Examination of Short-chain Peptides Related to SEQ ID NO:1 for Tumor Growth Inhibiting Effect In this test, three short-chain peptides having a partial sequence of the sequence shown in SEQ ID NO:1 or containing a partial sequence thereof, namely three peptides having the amino acid sequences shown below in Table 6, were synthesized by the solid phase method of peptide synthesis according to the method of Example 2 and used.

TABLE 6

| Amino acid sequence | Remarks |
| --- | --- |
| SEQ ID NO: 17 | 5-Residue peptide resulting from addition of Ala to the N terminus of positions 1 to 4 of SEQ ID NO: 1 |
| SEQ ID NO: 19 | 12-Residue peptide containing positions 1 to 8 of SEQ ID NO: 1 |
| SEQ ID NO: 20 | 8-Residue peptide comprising positions 8 to 15 of SEQ ID NO: 1 |

The three short-chain peptides synthesized and physiological saline as a control were respectively administered subcutaneously to mice on days 1 to 10 following tumor cell implantation according to the method of Example 4 (2), and the tumor growth inhibiting activities were examined. The results obtained are shown in FIG. 6 in the same manner as in FIG. 3.

In the figure, open circles are for the group given physiological saline, closed circles are for the group given the peptide shown in SEQ ID NO:19, open squares are for the group given the peptide shown in SEQ ID NO:17, and closed squares are for the group given the peptide shown in SEQ ID NO:20.

Figure 6:
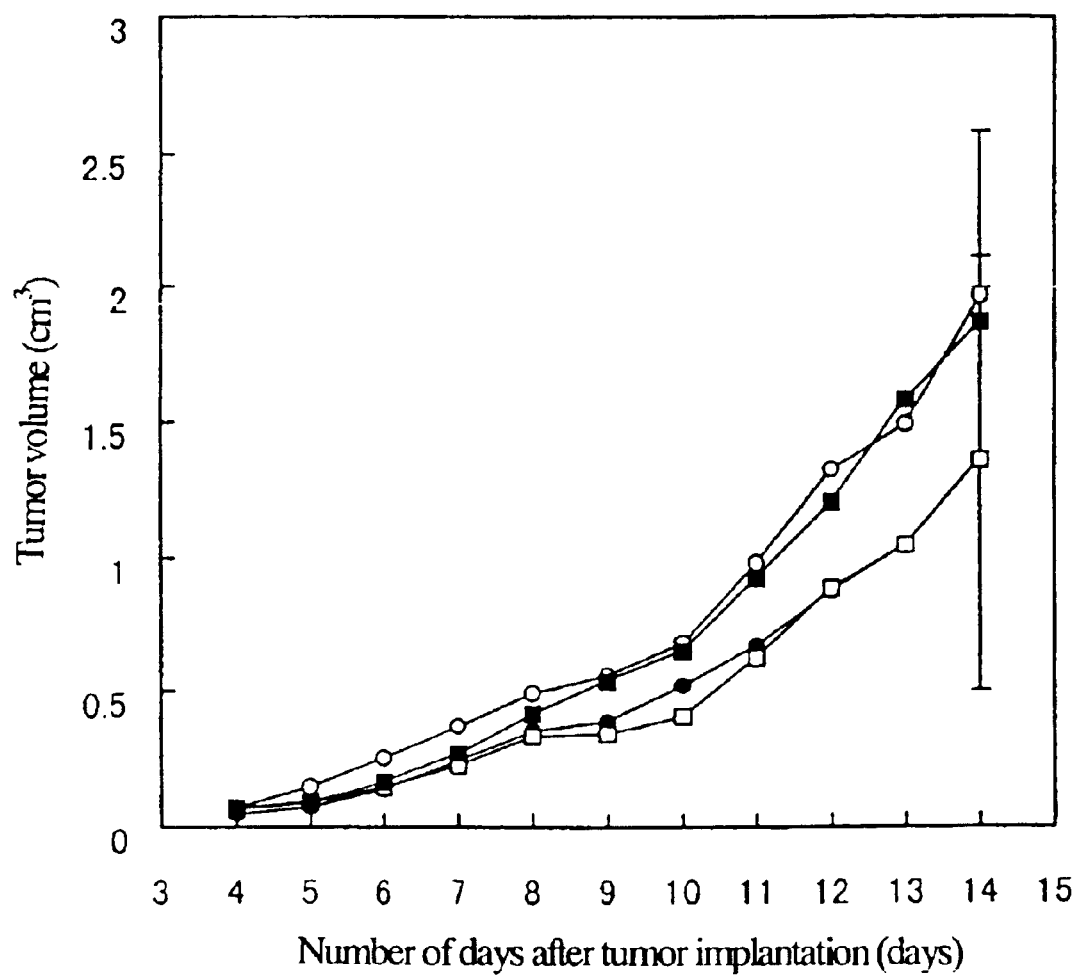
FIG. 6 is a graphic representation of the tumor growth inhibiting effects of the peptides of the invention shown in Example 6 (2).

From FIG. 6, a tendency toward inhibition of tumor growth was confirmed in the groups given the peptides containing PRP occurring in the first half of the sequence shown in SEQ ID NO:1 (the group given the peptide shown in SEQ ID NO:19 and the group given the peptide shown in SEQ ID NO:17).

(3) Examination of Short-chain Peptides Related to SEQ ID NO:5 for Tumor Growth Inhibiting Effect Peptides shown below in Table 7, namely a peptide having the whole sequence shown in SEQ ID NO:5, peptides having one of two partial sequences of SEQ ID NO:5 (peptide shown in SEQ ID NO:13 and peptide shown in SEQ ID NO:21) and a peptide (SEQ ID NO:22) resulting from replacement of an arbitrary sequence for the sequence shown in SEQ ID NO:5, were synthesized by the solid phase method of peptide synthesis according to the method of Example 2 and subjected to the test.

TABLE 7

| Amino acid sequence | Remarks |
| --- | --- |
| SEQ ID NO: 5 | 15-Residue peptide |
| SEQ ID NO: 13 | 8-Residue peptide comprising positions 1 to 8 of SEQ ID NO: 5 |
| SEQ ID NO: 21 | 8-Residue peptide comprising positions 8 to 15 of SEQ ID NO: 5 |
| SEQ ID NO: 22 | 15-Residue peptide resulting from arbitrary replacement for the sequence of SEQ ID NO: 5 |

A dose of 20 mg/kg/day of each of the peptides synthesized in the above manner or distilled water (DW) as a control was subcutaneously administered to mice on days 4 to 9 after tumor cell implantation according to the method of Example 4 (2), and the tumor growth inhibiting activities were examined. Three to five mice per group were used in the experiment. The results are shown in FIG. 7 in the same manner as in FIG. 3.

In the figure, open circles are for the group given distilled water, closed circles are for the group given the peptide shown in SEQ ID NO:5, open squares are for the group given the peptide shown in SEQ ID NO:22 (comparative group, namely the group given the 15-residue peptide resulting from arbitrary sequence replacement for SEQ ID NO:5), closed squares are for the group given the peptide shown in SEQ ID NO:13, and open triangles are for the group given the peptide shown in SEQ ID NO:21.

Figure 7:
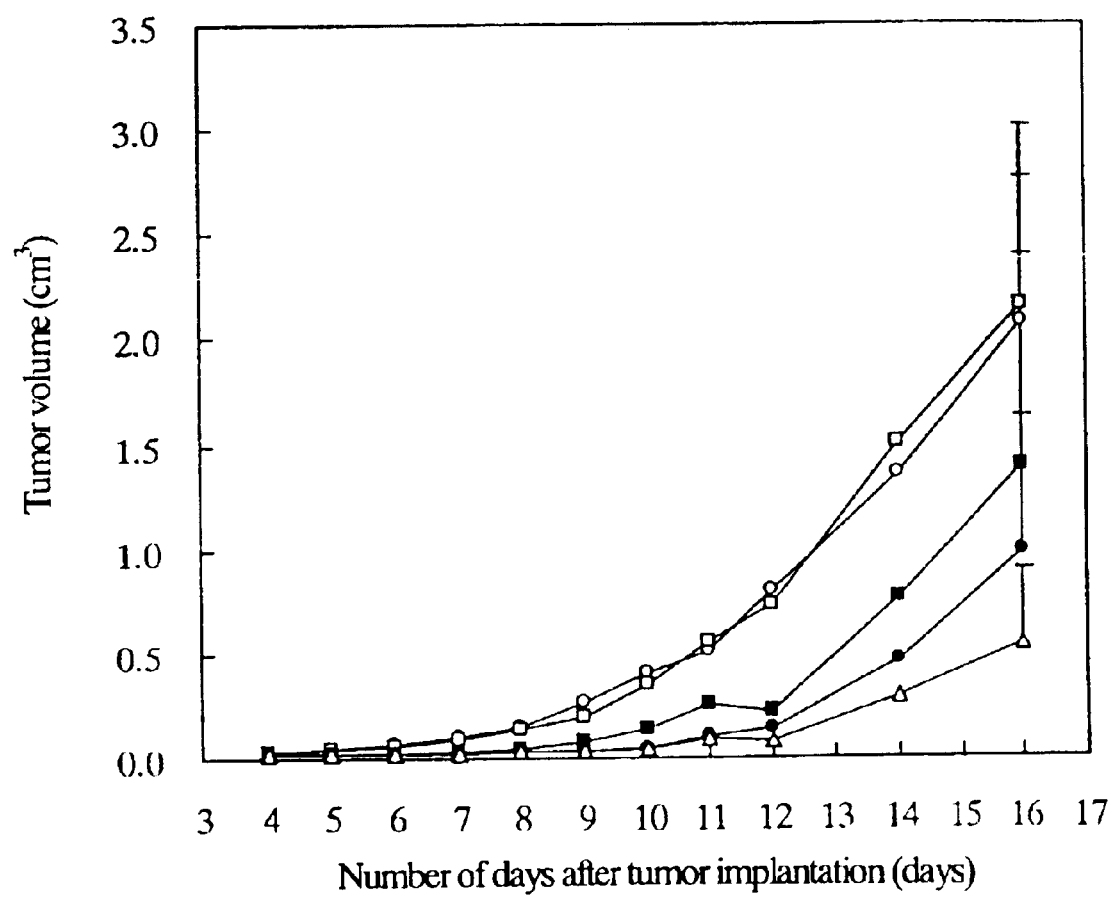
FIG. 7 is a graphic representation of the tumor growth inhibiting effects of the peptides of the invention shown in Example 6 (3).

From FIG. 7, it was confirmed that the peptide having the whole sequence shown in SEQ ID NO:5 and the short-chain peptides having the first half or last half of that sequence all have tumor growth inhibiting activity.

(4) Examination of Short-chain Peptides (5-Residue Peptides) Related to SEQ ID NO:5 for Tumor Growth Inhibiting Effect For further examining the effects of the peptide sequences on the activity producing tumor growth inhibiting effects in view of the results mentioned above under (3), three peptides having a partial sequence of SEQ ID NO:5, as shown below in Table 8, were synthesized by the solid phase method of peptide synthesis according to the method of Example 2 and subjected to the experiment.

TABLE 8

| Amino acid sequence | Remarks |
| --- | --- |
| SEQ ID NO: 23 | Peptide comprising positions 8 to 12 of SEQ ID NO: 5 |
| SEQ ID NO: 24 | Peptide comprising positions 11 to 15 of SEQ ID NO: 5 |
| SEQ ID NO: 25 | Peptide comprising positions 5 to 9 of SEQ ID NO: 5 |

A dose of 20 mg/kg/day of each of the peptides synthesized in the above manner or physiological saline as a control was subcutaneously administered to mice on days 1 to 10 after tumor cell implantation according to the method of Example 4 (2), and the tumor growth inhibiting activities were examined. Four or five mice per group were used in the experiment. The results are shown in FIG. 8 in the same manner as in FIG. 3.

In the figure, open circles are for the group given the peptide shown in SEQ ID NO:23, closed circles are for the group given the peptide shown in SEQ ID NO:24, open squares are for the group given the peptide shown in SEQ ID NO:25, and closed squares are for the group given physiological saline.

Figure 8:
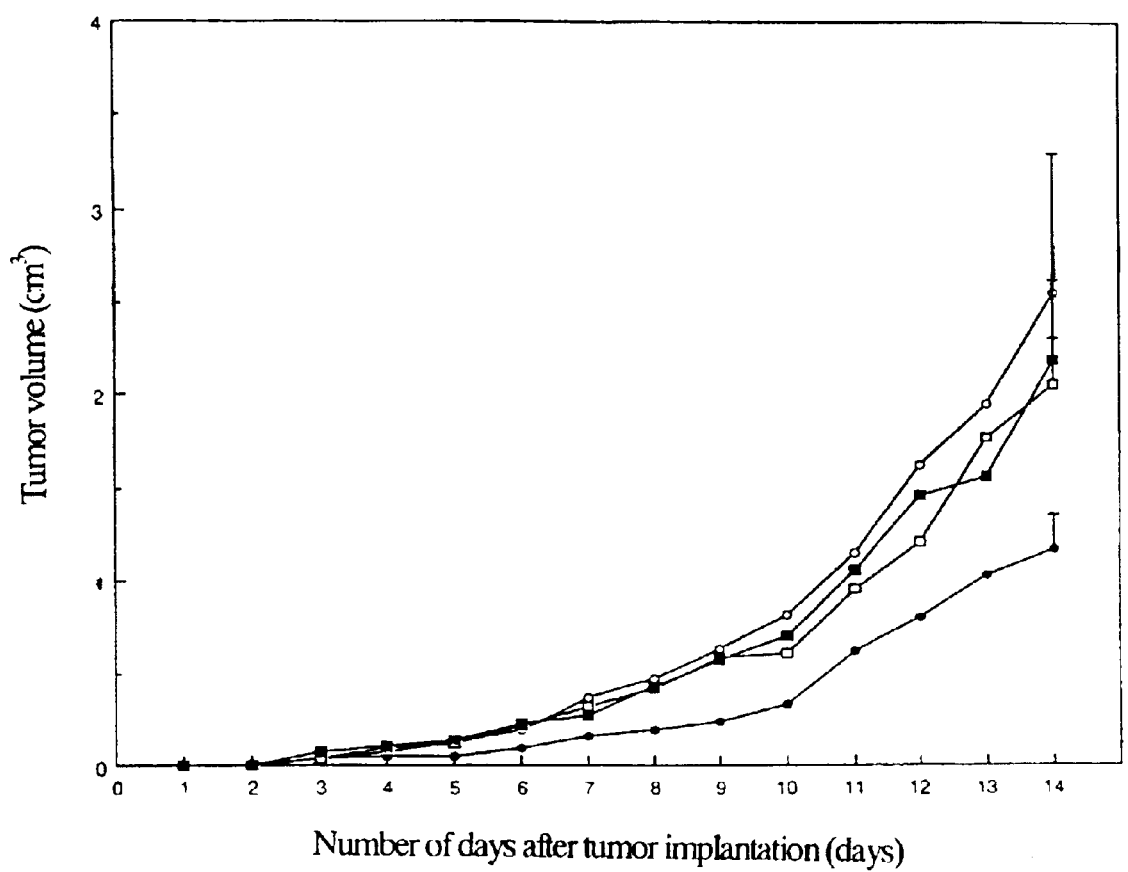
FIG. 8 is a graphic representation of the tumor growth inhibiting effects of the peptides of the invention shown in Example 6 (4).

From FIG. 8, it was confirmed that even the 5-residue short-chain peptide comprising positions 11 to 15 of SEQ ID NO:5 have antitumor activity.

(5) Examination of Short-chain Peptides Related to SEQ ID NO:6 for Tumor Growth Inhibiting Effect For examining the peptide sequences influencing the tumor growth inhibiting effect of short-chain peptides related to the peptide shown in SEQ ID NO:6 in the same manner as mentioned above under (3), the peptide shown in SEQ ID NO:6, three partial peptides thereof (SEQ ID NO:26, 14 and 16) and a comparative peptide (SEQ ID NO:27) derived from replacement of an arbitrary sequence for the sequence shown in SEQ ID NO:6 were synthesized by the solid phase method of peptide synthesis according to the method of Example 2 and used in the test.

TABLE 9

| Amino acid sequence | Remarks |
| --- | --- |
| SEQ ID NO: 6 | 15-Residue peptide |
| SEQ ID NO: 14 | 8-Residue peptide comprising positions 8 to |

TABLE 9-continued

| Amino acid sequence | Remarks |
|---|---|
| | 15 of SEQ ID NO: 6 |
| SEQ ID NO: 16 | 5-Residue peptide comprising positions 9 to 13 of SEQ ID NO: 6 |
| SEQ ID NO: 26 | 8-Residue peptide comprising positions 1 to 8 of SEQ ID NO: 6 |
| SEQ ID NO: 27 | 15-Residue peptide resulting from arbitrary substitution of the sequence shown in SEQ ID NO: 6 |

A dose of 20 mg/kg/day of each of the peptides synthesized in the above manner or distilled water as a control was subcutaneously administered to mice on days 1 to 10 after tumor cell implantation according to the method of Example 4 (2), and the tumor growth inhibiting activities were examined. Five or six mice per group were used in the experiment. The results are shown in FIG. 9 in the same manner as in FIG. 3.

In the figure, open circles are for the group given distilled water, closed circles are for the group given the peptide shown in SEQ ID NO:6, open squares are for the group given the peptide shown in SEQ ID NO:26, closed squares are for the group given the peptide shown in SEQ ID NO:14, open triangles are for the group given the peptide shown in SEQ ID NO:16, and closed triangles are for the group given the peptide shown in SEQ ID NO:27.

Figure 9:
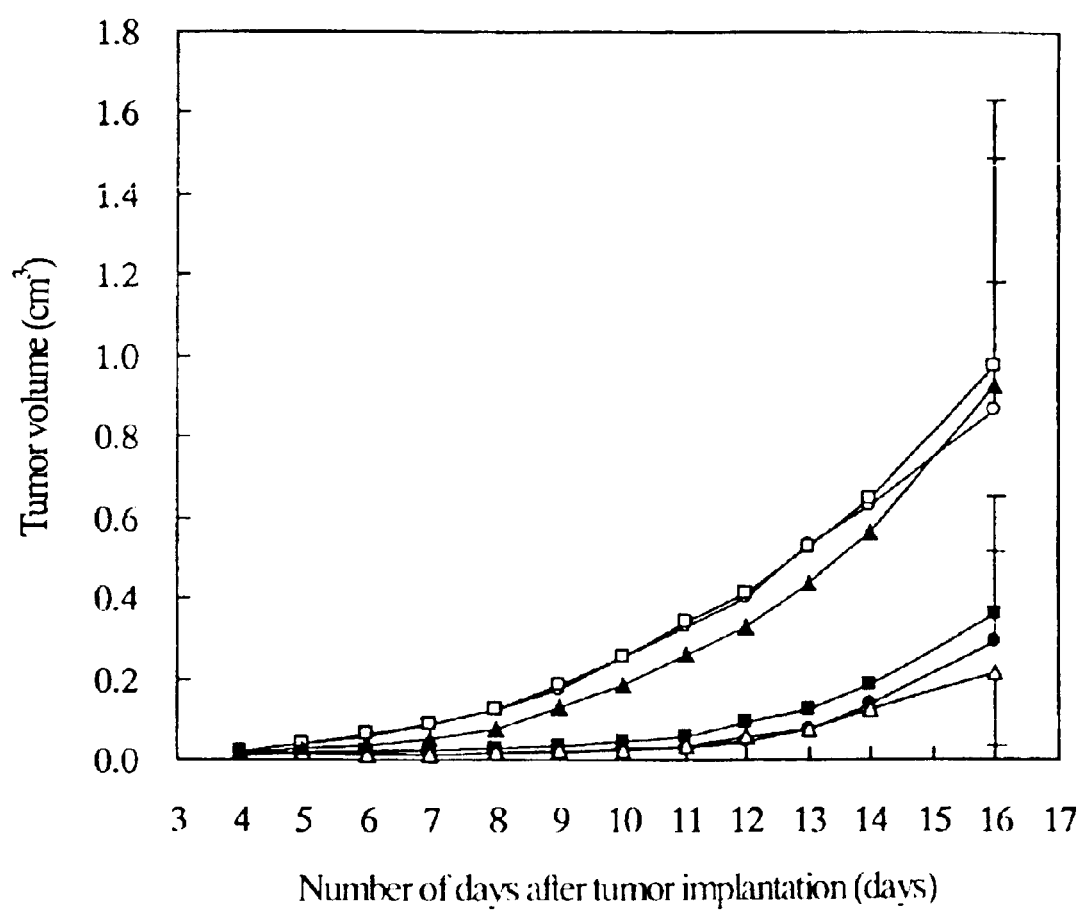
FIG. 9 is a graphic representation of the tumor growth inhibiting effects of the peptides of the invention shown in Example 6 (5).

From FIG. 9, it was confirmed that the short-chain peptides containing the sequence WRP have antitumor activity.

(6) Examination of Short-chain Peptides Containing WRP or Containing WRP by Substitution of One Residue Thereof for Tumor Growth Inhibiting Effect For further examining the importance of the sequence WRP for the antitumor activity in view of the results mentioned above under (5), 3- or 4-residue peptides containing the sequence WRP as derived from SEQ ID NO:5, SEQ ID NO:6 and both of SEQ ID NO:5 and 6 and 5-residue peptides resulting from substitution of alanine (A: Ala) for one of the amino acid residues in the sequence WRP, as shown below in Table 10, were synthesized by the solid phase method of peptide synthesis according to the method of Example 2 and used in the test.

TABLE 10

| Amino acid sequence | Remarks |
|---|---|
| SEQ ID NO: 28 | 4-Residue peptide comprising positions 2 to 5 of SEQ ID NO: 5 |
| SEQ ID NO: 29 | 4-Residue peptide comprising positions 9 to 12 of SEQ ID NO: 6 |
| SEQ ID NO: 30 | 4-Residue peptide comprising positions 3 to 12 of SEQ ID NO: 5 |
| SEQ ID NO: 31 | 4-Residue peptide comprising positions 10 to 13 of SEQ ID NO: 6 |
| SEQ ID NO: 32 | 3-Residue peptide common to SEQ ID NO: 5 and 6 |
| SEQ ID NO: 33 | Peptide derived from SEQ ID NO: 16 by substitution of A for W |
| SEQ ID NO: 34 | Peptide derived from SEQ ID NO: 16 by substitution of A for R |
| SEQ ID NO: 35 | Peptide derived from SEQ ID NO: 16 by substitution of A for P |

A dose of 20 mg/kg/day of each of the peptides synthesized in the above manner or distilled water or physiological saline as a control was subcutaneously administered to mice on days 1 to 10 after tumor cell implantation according to the method of Example 4 (2), and the tumor growth inhibiting activities were examined. Five or six mice per group were used in the experiment. The results are shown in FIG. 10 (results with the peptides of SEQ ID NO:28–32) and FIG. 11 (results with the peptides of SEQ ID NO:33–35) in the same manner as in FIG. 3.

Figure 10:
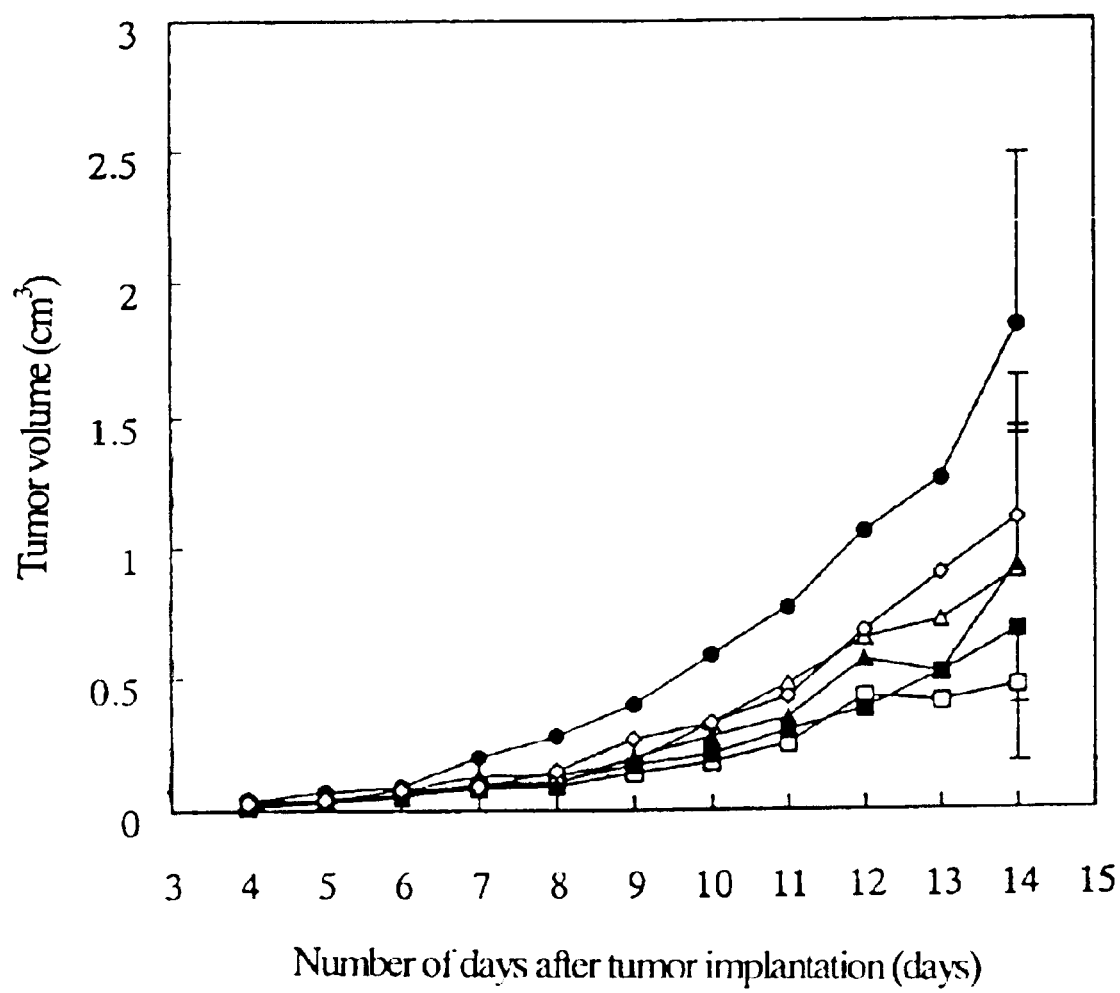
FIG. 10 and FIG. 11 each is a graphic representation of the tumor growth inhibiting effects of the peptides of the invention shown in Example 6 (6).

In FIG. 10, white rhombi are for the group given the peptide shown in SEQ ID NO:32, closed circles are for the group given distilled water, open squares are for the group given the peptide shown in SEQ ID NO:28, closed squares are for the group given the peptide shown in SEQ ID NO:29, open triangles are for the group given the peptide shown in SEQ ID NO:30, and closed triangles are for the group given the peptide shown in SEQ ID NO:31.

From the figure, it was confirmed that the short-chain peptides containing the sequence WRP each has antitumor activity, and it was revealed that the intensities of the antitumor activity are in the following order: peptide of SEQ ID NO:28=peptide of SEQ ID NO:29>peptide of SEQ ID NO:30=peptide of SEQ ID NO:31>peptide of SEQ ID NO:32.

Figure 11:
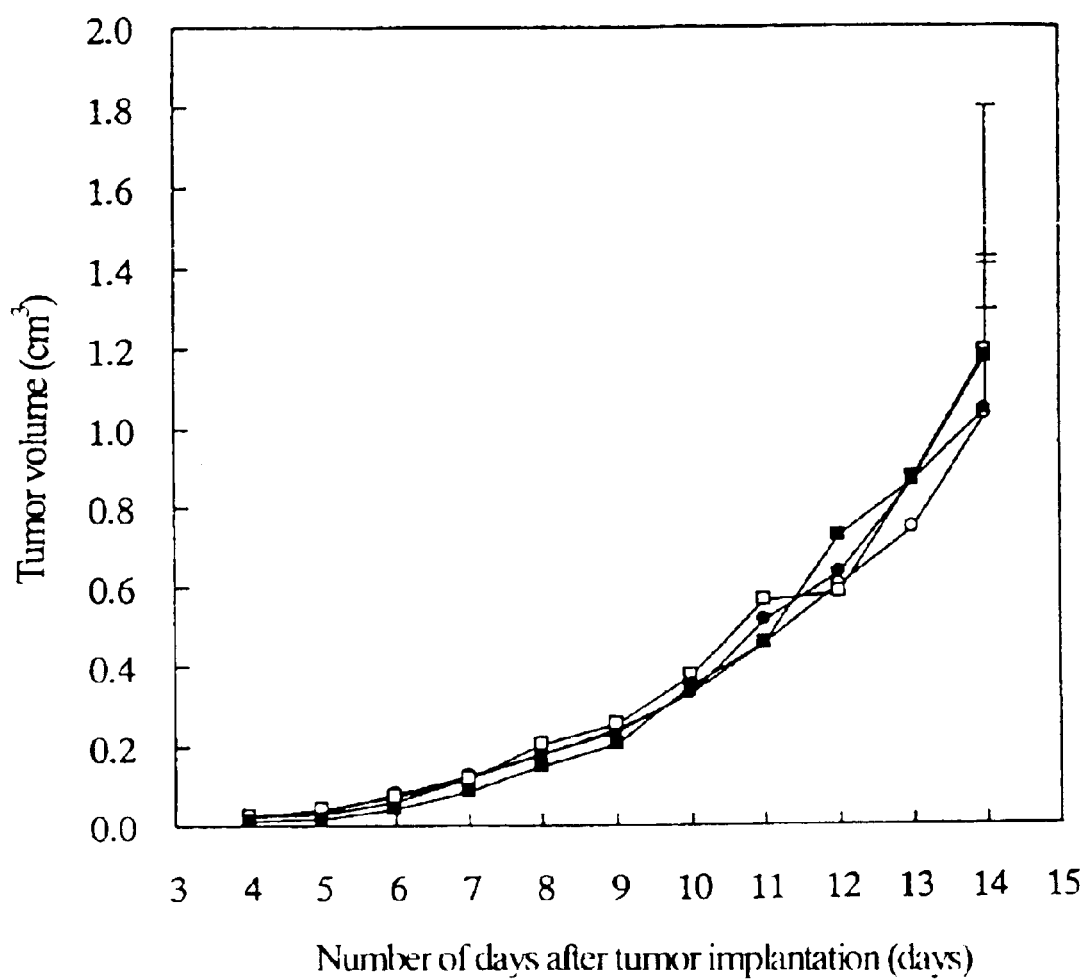

In FIG. 11, open circles are for the group given physiological saline, closed circles are for the group given the peptide shown in SEQ ID NO:33, open squares are for the group given the peptide shown in SEQ ID NO:34, and closed squares are for the group given the peptide shown in SEQ ID NO:35.

From FIG. 11, it was found that the short-chain peptides which do not contain the sequence WRP have no antitumor activity.

From the above results, it was established that the sequence WRP is important for a peptide to have antitumor activity and that short-chain peptides comprising 4 or 5 residues including said sequence WRP have antitumor activity.

EXAMPLE 7

Examination of Peptide-modified Liposomes (1) Examination of Peptide-modified Liposomes for Tumor Growth Inhibiting Effect Liposomes modified with the peptide having the sequence shown in SEQ ID NO:15, 16 or 17 were prepared in a similar manner as described in Example 5 (1) and examined for their tumor growth inhibiting effect. In preparing each peptide-modified liposome species, the addition of [oleate-1-$^{14}$C]-labeled cholesterol oleate was omitted.

Figure 12:
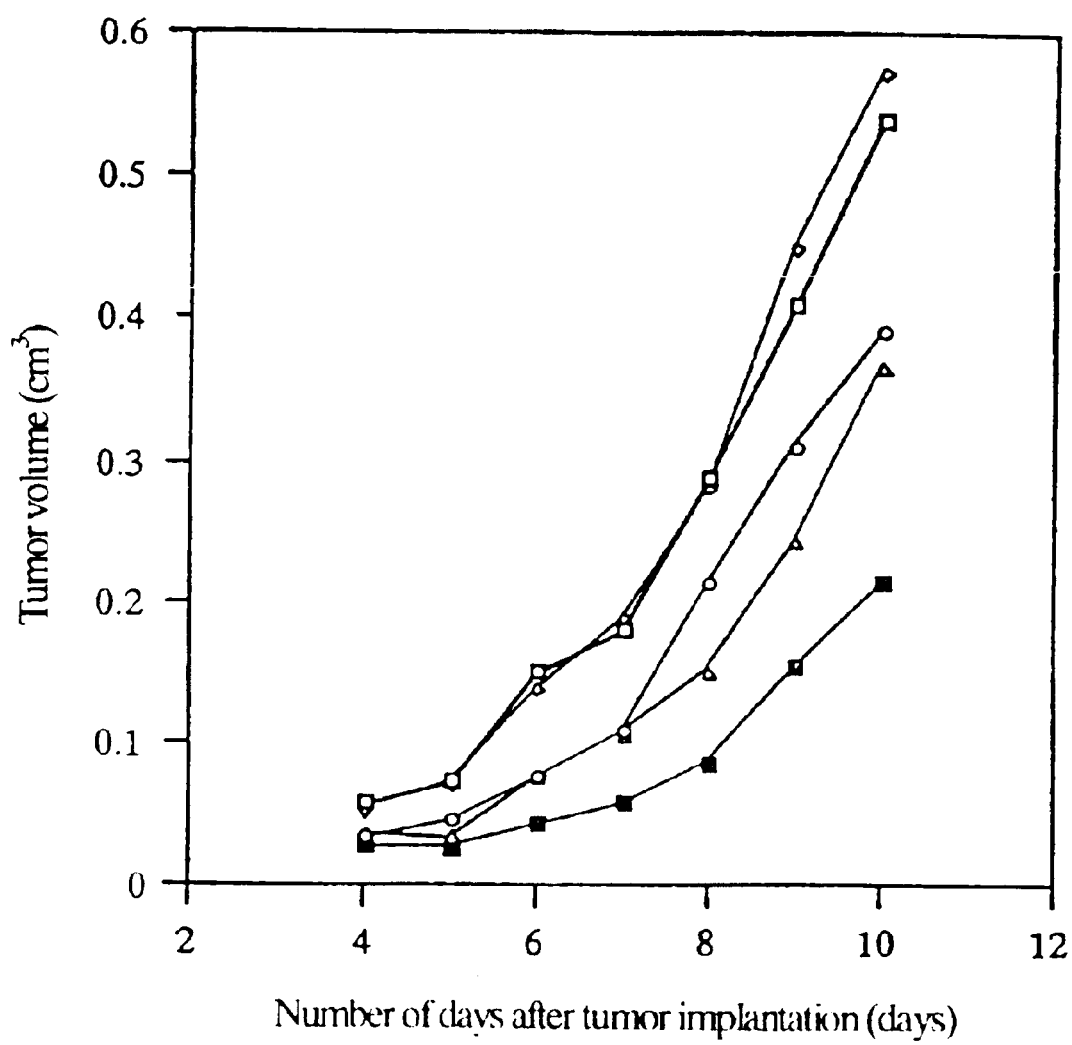
FIG. 12 is a graphic representation of the tumor growth inhibiting effects of the liposomes modified with the peptides of the invention as shown in Example 7 (1).

A dose of 20 mg/kg/day of each of the peptide-modified liposome dispersions, or physiological saline as a control or a control liposome dispersion (no peptide added) was subcutaneously administered to mice three times, namely on days 4, 6 and 8 after tumor cell implantation according to the method of Example 4 (2), and the tumor growth inhibiting activities of the respective peptide-modified liposomes were examined. Five mice per group were used in the experiment. The results are shown in FIG. 12 in the same manner as in FIG. 3.

In the figure, open rhombi are for the group given the control liposomes, open squares are for the group given physiological saline, open circles are for the group given the liposomes modified with the peptide shown in SEQ ID NO:17, open triangles are for the group given the liposomes modified with the peptide shown in SEQ ID NO:15, and closed squares are for the group given the liposomes modified with the peptide shown in SEQ ID NO:16.

From FIG. 12, it was revealed that the levels of antitumor effect are in the following order: liposomes modified with peptide of SEQ ID NO:15>liposomes modified moifiedwith peptide of SEQ ID NO:16>liposomes modified with peptide of SEQ ID NO: 17. From FIG. 12, it was also confirmed that these short-chain peptides containing the sequence WRP are more potent in antitumor activity.

(2) Influences of the Peptide Composition on the Affinity of Peptide-modified Liposomes for Tumor Tissue Based on the results of the test for in vivo distribution in Example 5, indicating that the liposomes modified with the peptide having the sequence shown in SEQ ID NO:17 were the most tumor-specific, the mole ratio of this peptide in the liposomes was varied to thereby examine the changes in specificity to tumor.

Thus, liposome dispersions were prepared in a similar manner as described in Example 5 (1). On that occasion, the lipid DSPC (distearoylphosphatidylcholine; product of Nippon Seika), cholesterol (product of Sigma) and the stearic acid derivative of the angiogenesis-specific peptide of the invention (SEQ ID NO:17: derived from the partial peptide shown in SEQ ID NO:1 by addition of Ala to the N terminus thereof) were used in mole ratios of 10:5:2 (hereinafter referred to PRP-20), 10:5:1 (hereinafter referred to PRP-10), 10:5:0.5 (hereinafter referred to PRP-5) and 10:5:0 (control liposomes; hereinafter referred to control). The liposome concentration was adjusted so that DSPC amounted to 5 mM, and the size was adjusted to 100 nm.

Then, each liposome dispersions prepared in the above manner was examined for the affinity for tumor tissue by a similar method of Example 5 (2). Two or three tumor-bearing mice per group were used in the test.

Figure 13:
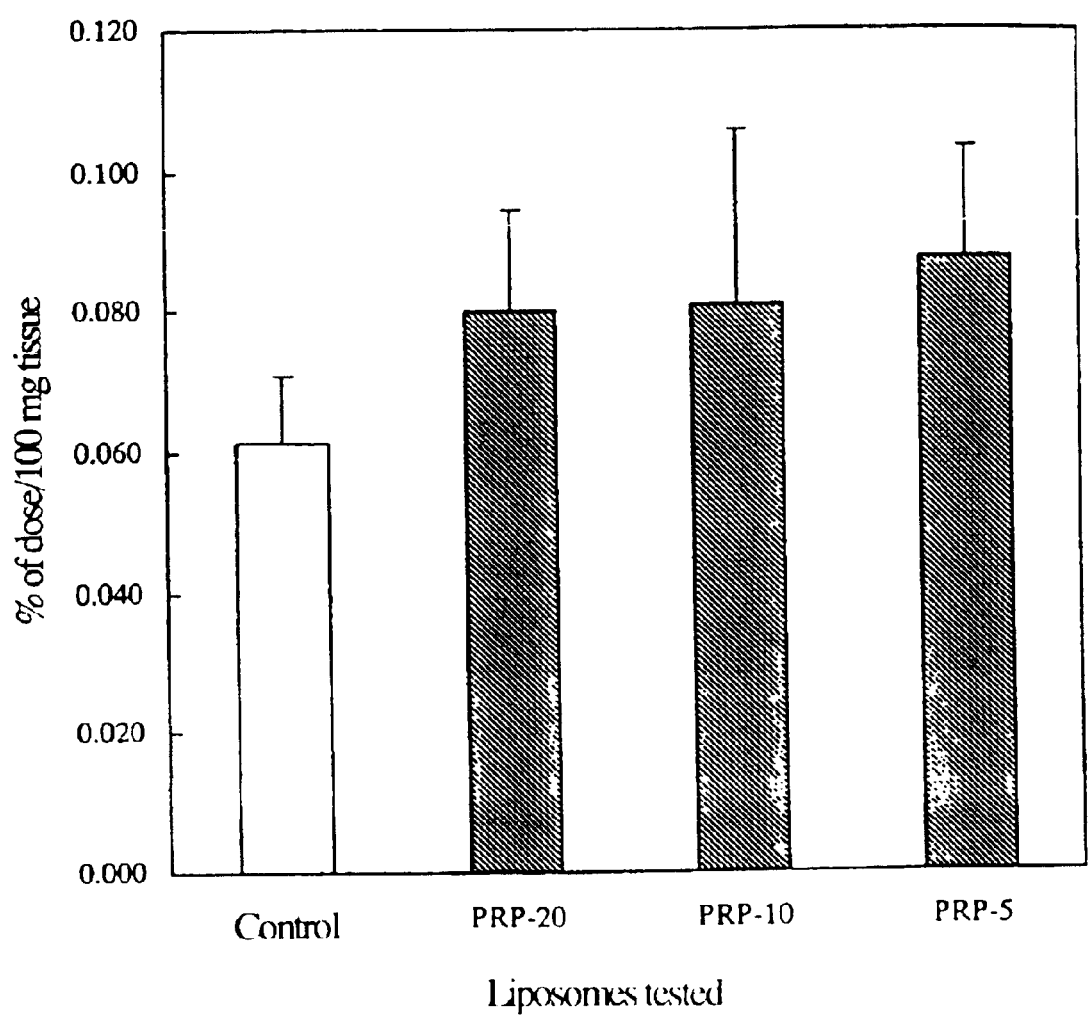
FIG. 13 is a graphic representation of the affinities of the liposomes modified with the peptides of the invention as shown in Example 7 (2) for tumor tissues.

The results are shown in FIG. 13 (ordinate: % of dose/100 mg tissue, abscissa: each liposome preparation tested) in the same manner as in FIG. 4.

From FIG. 13, it was found that even when the amount of the angiogenesis-specific peptide, one of the active ingredients of the liposome preparation of the invention, is lowered to 5 mole percent, the desired affinity for tumor is not influenced.

(3) Examination of Peptide-modified Liposomes for Stability in Serum

Using the peptide-modified liposomes prepared as mentioned above under (2), stabilities of the liposomes in serum were examined by measuring the degree of agglutination in the following manner.

Thus, a mixture of 0.15 ml of each liposome dispersion, 0.75 ml of uninactivated fetal bovine serum (product of JRH Bioscience) and 0.6 ml of 0.3 M glucose solution was prepared. As a control, a mixture of 0.15 ml of the liposome dispersion and 1.35 ml of 0.3 M glucose solution was prepared. Each mixture was incubated at 37° C. for 30 minutes and the absorbance at 450 nm was measured (using a DU-70 spectrometer, product of Beckman).

From the thus-obtained measured values, the degree of agglutination of each liposome dispersions were calculated according to the following formula:

Degree of agglutination=absorbance at 450 nm in the presence of serum (turbidity of liposome dispersion)/ absorbance at 450 nm in the absence of serum (in 0.3 M glucose solution) (turbidity of liposome dispersion)

Figure 14:
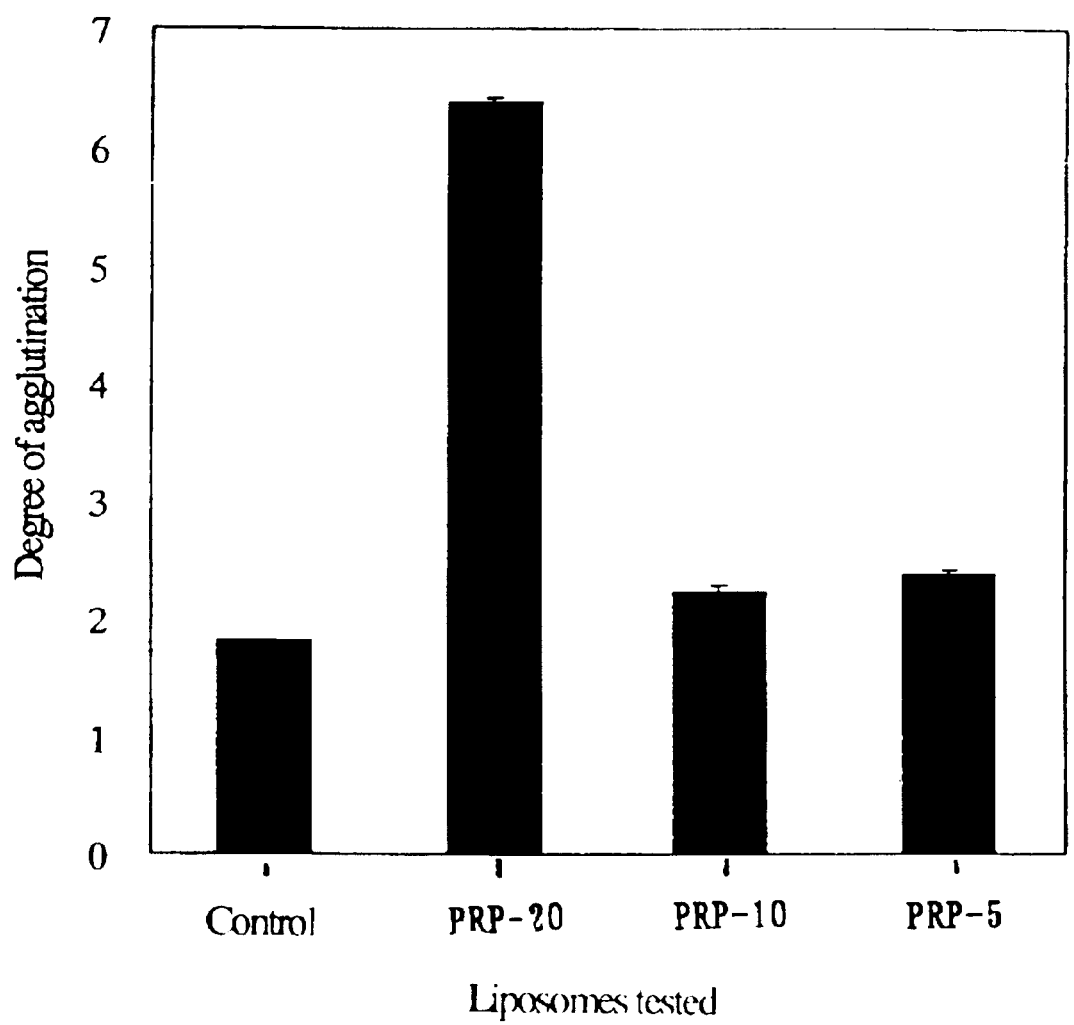
FIG. 14 is a graphic representation of the stabilities in blood of the liposomes modified with the peptides of the invention as shown in Example 7 (3).

The results obtained concerning the stability in serum (degree of agglutination) are shown in FIG. 14 (ordinate: degree of agglutination, abscissa: each liposome preparation tested)

From FIG. 14, it was confirmed that as far as the agglutination is concerned, the stability in serum of the liposome preparation of the invention is not influenced at least when the amount of the angiogenesis-specific peptide, one of the active ingredients of the liposome preparation of the invention, is not more than 10 mole percent.

EXAMPLE 8

Examination for Antitumor Effect of Liposome Preparations ID Containing the Angiogenesis-specific Peptide and an Anticancer Agent as Active Ingredients Based on the results of testing for influences on the affinity of the peptide-modified liposomes of the invention for tumor tissue as obtained in Example 7 (2), the liposomes mentioned below as prepared by including adriamycin, which is known as an anticancer agent, in peptide-modified liposomes containing 5 mole percent of the peptide shown in SEQ ID NO:17 were examined for their antitumor effect.

(1) Preparation of Peptide-modified Liposomes with Adriamycin (ADR) Included Therein For preparing a liposome solution, the stearic acid derivative of the angiogenesis-specific peptide of the invention (partial peptide, SEQ ID NO:17: derived from the partial peptide of SEQ ID NO:1 by addition of Ala to the N terminus thereof) was synthesized by the method of Example 2.

Then, a chloroform solution containing lipid DSPC (distearoylphosphatidylcholine; product of Nippon Seika), cholesterol (product of Sigma) and the above angiogenesis-specific peptide (stearic acid derivative of partial peptide) in the mole ratio of 10:5:0.5 was prepared. Thus, a chloroform solution containing the above ingredients in the mole ratio of 10:5:0.5 was prepared by admixing 400 µl of 100 mM DSPC, 200 µl of 100 mM cholesterol and 100 µl of the peptide of the invention (20 mM). Then, the solution prepared in the above manner was placed in a round-bottom flask and a thin lipid film was prepared by removing the chloroform under reduced pressure using a rotary evaporator. Further, the chloroform was completely removed under reduced pressure and the thin film was dried. After 60 minutes of drying under vacuum, the film was hydrated with 1 ml of 0.3 M citric acid solution (pH 4.0) (DSPC concentration: 40 mM).

The solution prepared in the above manner was subjected to three repetitions of freezing and thawing by warming at 70° C. and the solution prepared was then sonicated with stirring for 10 minutes using a warm bath type sonicator (trademark: ULTRASONIK 250; product of Labosco). Then, using an extruder (product of Lipex), the solution was passed through a polycarbonate membrane (Nucleopore polycarbonate; product of Coaster) having 100-nm pores three times to give the desired liposomes (dispersion) containing the molecule resulting from coupling of stearic acid to the N terminus of the angiogenesis-specific peptide (partial peptide) of the invention. In the product, the partial peptide is in a form modifying the liposome surface.

The aqueous phase exterior to liposomes was adjusted to pH 7.5 by adding 0.5 M sodium carbonate solution to the liposome dispersion. Then, the dispersion was diluted with 20 mM HEPES buffer to make the whole amount 2.0 ml. Further, 0.58 ml of a 10 mg/ml solution of adriamycin (product of Sigma) was added, and the mixture was incubated at 60° C. for 1 hour to thereby cause adriamycin to be included in the aqueous layer inside liposomes.

The resulting dispersion was centrifuged for 5 minutes (CS120EX, product of Hitachi Koki; 100,000 g) to precipitate liposomes and remove the supernatant containing the unincluded portion of adriamycin. The sediment was redispersed in 1 ml of 0.3 M glucose solution and the amount of adriamycin included was determined by the assay method mentioned below. Then the dispersion was diluted to an adriamycin concentration of 1.1 mg/ml (10 mg/kg) giving an angiogenesis-specific liposome preparation (dispersion) of the invention with adriamycin included in the liposomes.

Thus, liposomes (dispersion) containing DSPC, cholesterol and the angiogenesis-specific peptide (SEQ ID NO:17) of the invention in respective amounts of 40 μM, 20 μM and 2 μM in 5.5 ml (DSPC concentration: 7.3 mM) were obtained.

(2) Adriamycin Assaying (a) Construction of a Standard Curve for Adriamycin Assaying Mixtures of 0 μl, 100 μl, 200 μl and 400 μl of a 0.2 mg/ml adriamycin solution, 900 μl, 800 μl, 700 μl and 500 μl, respectively, of a 0.3 M glucose solution, and 100 μl of 10% reduced Triton X-100 (product of Aldrich) were measured for absorbance at 480 nm (Beckman DU-70 spectrometer) and a standard curve was obtained.

(b) Assay of Adriamycin in the Aqueous Layer Within Liposomes

The liposome dispersion (10 μl), 100 μl of 10% reduced Triton X-100 and 890 μl of a 0.3 M glucose solution were mixed up and then warmed at 60° C. and the absorbance at 480 nm was measured.

Using the thus-obtained measured value and the standard curve, the inclusion percentage of adriamycin in the aqueous layer within liposomes was calculated. The inclusion percentage was not less than 90%.

(3) Antitumor Effect of the Liposomes Modified with the Peptide of the Invention with Adriamycin Included Therein Solid tumor-bearing mice were prepared by subcutaneously administering Meth A sarcoma cells (1×106 cells/mouse) into the left flank of five-week-old BALB/c male mice (Japan SLC). The day of implantation was taken as day 1 and, on days 6, 9 and 12, the 0.3 M glucose solution (solvent) as a control, adriamycin (ADR)-including control liposomes (liposomes including the anticancer agent but free of any angiogenesis-specific peptide of the invention), a free ADR solution prepared by dissolving the anticancer agent ADR in a concentration of 15 mg/kg (mouse) in 0.3 M glucose, and the ADR-including, angiogenesis-specific peptide-modified liposomes of the invention as prepared above in (1) were respectively administered into the tail vein. In the test, 5 tumor-bearing mice were used in each group.

The antitumor effect of each agent administered was evaluated by examining, from 5 days after tumor implantation, the tumor volume as an indicator of tumor growth and the mouse body weight change as well as the survival period (days) as an indicator of side effect, in a similar manner as in Example 4 (2).

Figure 15:
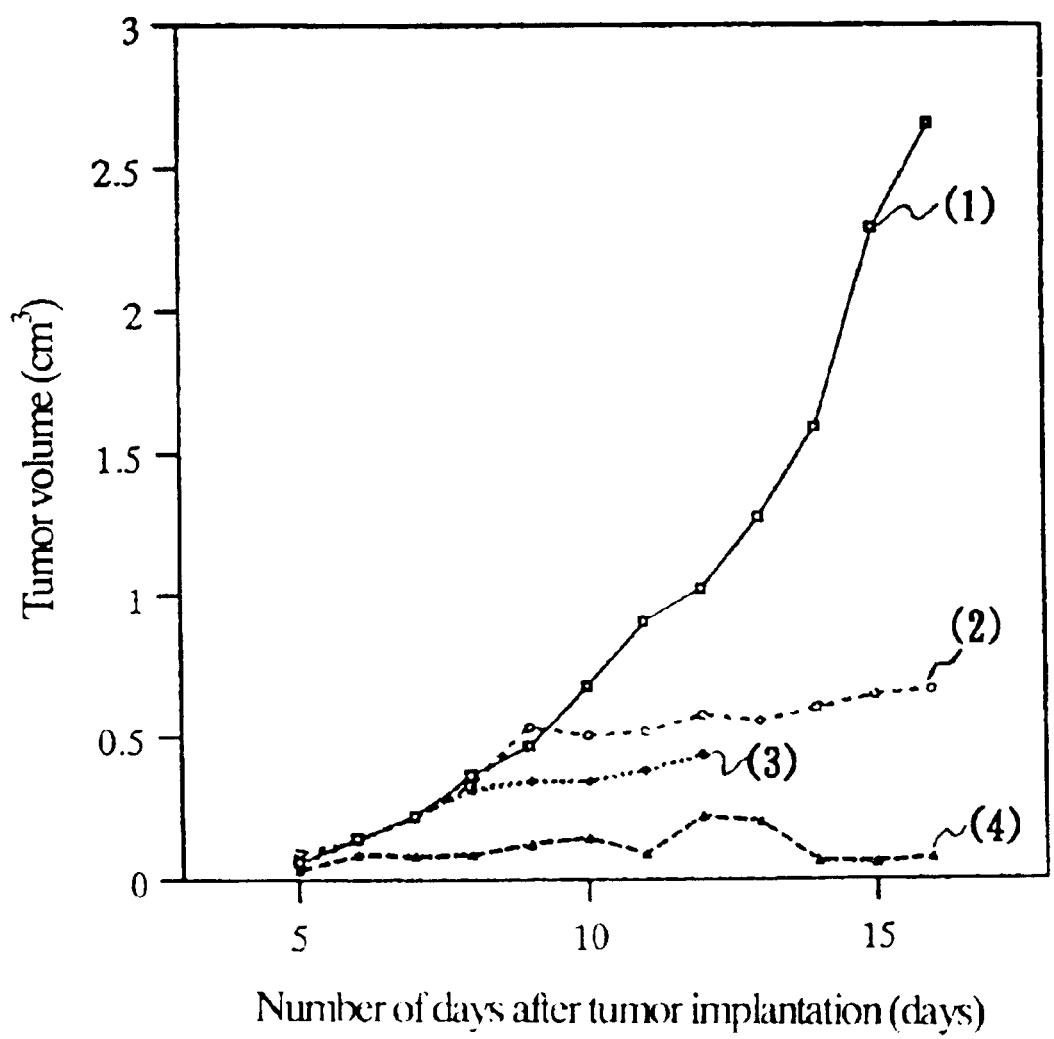
FIG. 15 is a graphic representation of the tumor growth inhibiting effects of the liposomes containing the angiogenesis-specific peptide of the invention and an anticancer agent as active ingredients according to Example 8.

The results are shown in FIG. 15.

In the figure, the ordinate denotes the tumor volume and the ascissa denotes the number of days after tumor implantation. In the figure, (1) is for the solvent group, (2) for the ADR-including control liposome group, (3) for the free ADR solution group and (4) for the group given the ADR-including, angiogenesis-specific peptide-modified liposomes of the invention.

As is evident from FIG. 15, all mice died after the three administrations on days 6, 9 and 12 in the group given the free (without inclusion in liposomes) adriamycin (ADR) solution (group (3)) whereas, in the group given adriamycin included in liposomes (group (2)), the death of mice was avoided. It was also revealed that, in the group given the adriamycin-including, angiogenesis-specific peptide-modified liposomes of the invention (group (4)), the growth of tumors implanted was markedly inhibited.

From the above results, it was established that, with the liposome preparation derived from peptide-modified liposomes containing the angiogenesis-specific peptide of the invention as an active ingredient by inclusion of the anticancer agent therein, the side effect of the anticancer agent included is reduced and the tumor growth inhibiting effect is markedly enhanced.

INDUSTRIAL APPLICABILITY

According to the invention, a novel angiogenesis-specific peptide is provided and, by utilizing said angiogenesis-specific peptide, it is possible to apply the same as a molecular drug serving as a ligand for angiogenic endothelial cells of the tumor tissue in DDS preparations enabling selective drug delivery to the target tissue and to provide a cancer diagnostic agent, a method of cancer diagnosis, a method of cancer therapy and the like to thereby contribute to improvements in cancer therapy efficiency.

What is claimed is:

1. An isolated angiogenesis-specific peptide selectively homing to neovascular tissues, wherein said peptide is selected from the group consisting of a peptide consisting of the sequence of SEQ ID NO:13 or a dendrimer thereof, a peptide consisting of the sequence of SEQ ID NO:14 or a dendrimer thereof, a peptide consisting of the sequence of SEQ ID NO:15 or a dendrimer thereof, a peptide consisting of the sequence of SEQ ID NO:16 or a dendrimer thereof and a peptide consisting of the sequence of SEQ ID NO:17 or a dendrimer thereof.

2. A cancer-inhibiting or cancer metastasis-inhibiting composition comprising:

(A) an effective amount of a peptide consisting of the sequence of SEQ ID NO:13 or a dendrimer thereof, a peptide consisting of the sequence of SEQ ID NO:14 or a dendrimer thereof, a peptide consisting of the sequence of SEQ ID NO:15 or a dendrimer thereof, a peptide consisting of the sequence of SEQ ID NO:16 or a dendrimer thereof and a peptide consisting of the sequence of SEQ ID NO:17 or a dendrimer thereof; and (B) a pharmaceutically acceptable carrier.

* * * * *

SEQUENCE LISTING

```
<160> NUMBER OF SEQ ID NOS: 35

<210> SEQ ID NO 1
<211> LENGTH: 15
<212> TYPE: PRT
<213> ORGANISM: phage library

<400> SEQUENCE: 1

Pro Arg Pro Gly Ala Pro Leu Ala Gly Ser Trp Pro Gly Thr Ser
1               5                   10                  15

<210> SEQ ID NO 2
<211> LENGTH: 15
<212> TYPE: PRT
<213> ORGANISM: phage library
<220> FEATURE:
<221> NAME/KEY: misc_feature
<223> OTHER INFORMATION: "Xaa" may be any amino acid
```

```
<400> SEQUENCE: 2

Ala Xaa Glu Trp Leu Asp Ala Leu Phe Val Arg His Val Asp Arg
1               5                   10                  15

<210> SEQ ID NO 3
<211> LENGTH: 15
<212> TYPE: PRT
<213> ORGANISM: phage library

<400> SEQUENCE: 3

Ala Ala Glu Trp Leu Asp Ala Phe Phe Val Arg His Val Asp Arg
1               5                   10                  15

<210> SEQ ID NO 4
<211> LENGTH: 15
<212> TYPE: PRT
<213> ORGANISM: phage library

<400> SEQUENCE: 4

Ala Pro Cys Cys Ser His Leu Asp Ala Ser Pro Phe Gln Arg Pro
1               5                   10                  15

<210> SEQ ID NO 5
<211> LENGTH: 15
<212> TYPE: PRT
<213> ORGANISM: phage library

<400> SEQUENCE: 5

Asp Arg Trp Arg Pro Ala Leu Pro Val Val Leu Phe Pro Leu His
1               5                   10                  15

<210> SEQ ID NO 6
<211> LENGTH: 15
<212> TYPE: PRT
<213> ORGANISM: phage library

<400> SEQUENCE: 6

Ala Ser Ser Ser Tyr Pro Leu Ile His Trp Arg Pro Trp Ala Arg
1               5                   10                  15

<210> SEQ ID NO 7
<211> LENGTH: 15
<212> TYPE: PRT
<213> ORGANISM: phage library

<400> SEQUENCE: 7

Arg Ala Ser Asp Val Gly Ser Asp Val Val Pro Arg Tyr Pro Phe
1               5                   10                  15

<210> SEQ ID NO 8
<211> LENGTH: 15
<212> TYPE: PRT
<213> ORGANISM: phage library
<220> FEATURE:
<221> NAME/KEY: misc_feature
<223> OTHER INFORMATION: "Xaa" may be any amino acid

<400> SEQUENCE: 8

Xaa Phe Ala Arg Ala Pro Val Glu His His Asp Val Val Gly Leu
1               5                   10                  15

<210> SEQ ID NO 9
<211> LENGTH: 15
<212> TYPE: PRT
<213> ORGANISM: phage library
```

-continued

<400> SEQUENCE: 9

Gly Asp Val Trp Leu Phe Leu Thr Ser Thr Ser His Phe Ala Arg
1               5                   10                  15

<210> SEQ ID NO 10
<211> LENGTH: 15
<212> TYPE: PRT
<213> ORGANISM: phage library

<400> SEQUENCE: 10

Pro Ala Gln Ser Asn Phe Val Thr Trp Gly Tyr Asn Val Ala Val
1               5                   10                  15

<210> SEQ ID NO 11
<211> LENGTH: 15
<212> TYPE: PRT
<213> ORGANISM: phage library

<400> SEQUENCE: 11

Glu Gly Cys Ser Val Ser Ser Val Gly Ala Leu Cys Thr His Val
1               5                   10                  15

<210> SEQ ID NO 12
<211> LENGTH: 8
<212> TYPE: PRT
<213> ORGANISM: phage library

<400> SEQUENCE: 12

Ser Val Ser Ser Val Gly Ala Leu
1               5

<210> SEQ ID NO 13
<211> LENGTH: 8
<212> TYPE: PRT
<213> ORGANISM: phage library

<400> SEQUENCE: 13

Asp Arg Trp Arg Pro Ala Leu Pro
1               5

<210> SEQ ID NO 14
<211> LENGTH: 8
<212> TYPE: PRT
<213> ORGANISM: phage library

<400> SEQUENCE: 14

Ile His Trp Arg Pro Trp Ala Arg
1               5

<210> SEQ ID NO 15
<211> LENGTH: 5
<212> TYPE: PRT
<213> ORGANISM: phage library

<400> SEQUENCE: 15

Arg Trp Arg Pro Ala
1               5

<210> SEQ ID NO 16
<211> LENGTH: 5
<212> TYPE: PRT
<213> ORGANISM: phage library

<400> SEQUENCE: 16

```
His Trp Arg Pro Trp
1               5

<210> SEQ ID NO 17
<211> LENGTH: 5
<212> TYPE: PRT
<213> ORGANISM: phage library

<400> SEQUENCE: 17

Ala Pro Arg Pro Gly
1               5

<210> SEQ ID NO 18
<211> LENGTH: 15
<212> TYPE: PRT
<213> ORGANISM: phage library

<400> SEQUENCE: 18

Pro Ser Gly Gly Pro Leu Pro Thr Trp Ala Ala Arg Ser Pro Gly
1               5                   10                  15

<210> SEQ ID NO 19
<211> LENGTH: 12
<212> TYPE: PRT
<213> ORGANISM: phage library

<400> SEQUENCE: 19

Ala Asp Gly Ala Pro Arg Pro Gly Ala Pro Leu Ala
1               5                   10

<210> SEQ ID NO 20
<211> LENGTH: 8
<212> TYPE: PRT
<213> ORGANISM: phage library

<400> SEQUENCE: 20

Ala Gly Ser Trp Pro Gly Thr Ser
1               5

<210> SEQ ID NO 21
<211> LENGTH: 7
<212> TYPE: PRT
<213> ORGANISM: phage library

<400> SEQUENCE: 21

Pro Val Val Leu Phe Leu His
1               5

<210> SEQ ID NO 22
<211> LENGTH: 15
<212> TYPE: PRT
<213> ORGANISM: phage library

<400> SEQUENCE: 22

Leu Asp Leu Pro Leu Pro His Arg Pro Phe Val Arg Trp Ala Val
1               5                   10                  15

<210> SEQ ID NO 23
<211> LENGTH: 5
<212> TYPE: PRT
<213> ORGANISM: phage library

<400> SEQUENCE: 23

Pro Val Val Leu Phe
```

```
<210> SEQ ID NO 24
<211> LENGTH: 5
<212> TYPE: PRT
<213> ORGANISM: phage library

<400> SEQUENCE: 24

Leu Phe Pro Leu His
1               5

<210> SEQ ID NO 25
<211> LENGTH: 5
<212> TYPE: PRT
<213> ORGANISM: phage library

<400> SEQUENCE: 25

Pro Ala Leu Pro Val
1               5

<210> SEQ ID NO 26
<211> LENGTH: 8
<212> TYPE: PRT
<213> ORGANISM: phage library

<400> SEQUENCE: 26

Ala Ser Ser Ser Tyr Pro Leu Ile
1               5

<210> SEQ ID NO 27
<211> LENGTH: 15
<212> TYPE: PRT
<213> ORGANISM: phage library

<400> SEQUENCE: 27

Ser Ala Tyr Pro Ala Leu Ser Trp Ser His Arg Arg Ile Trp Pro
1               5                  10                  15

<210> SEQ ID NO 28
<211> LENGTH: 4
<212> TYPE: PRT
<213> ORGANISM: phage library

<400> SEQUENCE: 28

Arg Trp Arg Pro
1

<210> SEQ ID NO 29
<211> LENGTH: 4
<212> TYPE: PRT
<213> ORGANISM: phage library

<400> SEQUENCE: 29

His Trp Arg Pro
1

<210> SEQ ID NO 30
<211> LENGTH: 4
<212> TYPE: PRT
<213> ORGANISM: phage library

<400> SEQUENCE: 30

Trp Arg Pro Ala
1
```

```
<210> SEQ ID NO 31
<211> LENGTH: 4
<212> TYPE: PRT
<213> ORGANISM: phage library

<400> SEQUENCE: 31

Trp Arg Pro Trp
1

<210> SEQ ID NO 32
<211> LENGTH: 3
<212> TYPE: PRT
<213> ORGANISM: phage library

<400> SEQUENCE: 32

Trp Arg Pro
1

<210> SEQ ID NO 33
<211> LENGTH: 5
<212> TYPE: PRT
<213> ORGANISM: phage library

<400> SEQUENCE: 33

His Ala Arg Pro Trp
1               5

<210> SEQ ID NO 34
<211> LENGTH: 5
<212> TYPE: PRT
<213> ORGANISM: phage library

<400> SEQUENCE: 34

His Trp Ala Pro Trp
1               5

<210> SEQ ID NO 35
<211> LENGTH: 5
<212> TYPE: PRT
<213> ORGANISM: phage library

<400> SEQUENCE: 35

His Trp Arg Ala Trp
1               5
```